US011820987B2

(12) United States Patent
Alper et al.

(10) Patent No.: US 11,820,987 B2
(45) Date of Patent: Nov. 21, 2023

(54) COMPOSITIONS AND METHODS FOR TYPE III POLYKETIDE PRODUCTION IN OLEAGINOUS YEAST SPECIES

(71) Applicant: BOARD OF REGENTS, THE UNIVERSITY OF TEXAS SYSTEM, Austin, TX (US)

(72) Inventors: Hal Alper, Austin, TX (US); Kelly Markham, Austin, TX (US); Claire Palmer, Madison, WI (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/084,403

(22) PCT Filed: Mar. 14, 2017

(86) PCT No.: PCT/US2017/022252
§ 371 (c)(1),
(2) Date: Sep. 12, 2018

(87) PCT Pub. No.: WO2017/160801
PCT Pub. Date: Sep. 21, 2017

(65) Prior Publication Data
US 2019/0078098 A1   Mar. 14, 2019

Related U.S. Application Data

(60) Provisional application No. 62/307,912, filed on Mar. 14, 2016.

(51) Int. Cl.
| | | |
|---|---|---|
| C12N 15/52 | (2006.01) | |
| C12N 15/81 | (2006.01) | |
| C12N 9/10 | (2006.01) | |
| C12P 17/06 | (2006.01) | |

(52) U.S. Cl.
CPC ........... *C12N 15/52* (2013.01); *C12N 9/1029* (2013.01); *C12N 15/815* (2013.01); *C12P 17/06* (2013.01); *C12Y 203/01* (2013.01)

(58) Field of Classification Search
None
See application file for complete search history.

(56) References Cited

U.S. PATENT DOCUMENTS

| | | |
|---|---|---|
| 2006/0183211 A1 | 8/2006 | Kuzuyama et al. |
| 2014/0315269 A1 | 10/2014 | Delage et al. |
| 2014/0329287 A1 | 11/2014 | Blazeck et al. |

FOREIGN PATENT DOCUMENTS

| | | |
|---|---|---|
| WO | 2006/125000 A2 | 11/2006 |
| WO | 2014179748 | 11/2014 |
| WO | 2016198623 | 12/2016 |

OTHER PUBLICATIONS

Liu, L., et al. Genome Announc. Jul.-Aug. 2014; 2(4): e00652-14. (2 pages). (Year: 2014).*
Ledesma-Amaro, R., et al. 2016 Progress in Lipid Research 61: 40-50 (available online Dec. 15, 2015). (Year: 2015).*
UniProtKB—Q6C181 Glycogen [starch] synthase YALI0_F18502 gene 2004: 7 pages. (Year: 2004).*
Shi, S., et al. 2017 Frontiers in Microbiology vol. 8 Article 2185: 1-16. (Year: 2017).*
Extended European Search Report issued for Application No. 17767312.6, dated Sep. 30, 2019.
Donnez, David, et al. "Bioproduction of resveratrol and stilbene derivatives by plant cells and microorganisms." Trends in biotechnology 27.12 (2009): 706-713.
Abe, et al., The first plant type III polyketide synthase that catalyzes formation of aromatic heptaketide, FEBS Lett. Mar. 26, 2004;562(1-3):171-6.
Altschul et al. Basic local alignment search tool, J. Mol. Biol. 1990, 215:403-410.
Altschul et al. Gapped BLAST and PSI-BLAST: a new generation of protein database search programs, Nuc. Acids Res. 1997, 25:3389-3402.
Blazeck, J. et al. Harnessing Yarrowia lipolytica lipogenesis to create a platform for lipid and biofuel production, Nat Commun. 2014 5:3131.
Blazeck, J. et al. Heterologous production of pentane in the oleaginous yeast Yarrowia lipolytica, J Biotechnol. Jun. 2013 165(3-4):184-94.
Blazeck, J. et al. Metabolic engineering of Yarrowia lipolytica for itaconic acid production. Metab Eng. Nov. 2015 32:66-73.
Borejsza-Wysocki, et al, Aromatic Polyketide Synthases (Purification, Characterization, and Antibody Development to Benzalacetone Synthase from Raspberry Fruits), Plant Physiol. 1996, 791-799.
Eckermann, et al., New pathway to polyketides in plants, Nature 396(6709):387-390, 1998.
Henikoff and Henikoff (1989) Amino acid substitution matrices from protein blocks, Proc. Natl. Acad. Sci. USA 1989, 89:10915-10919.
Karlin and Altschul, Applications and statistics for multiple high-scoring segments in molecular sequences. Proc. Natl. Acad. Sci. USA 1993, 90:5873-5787.
Katsuyama, et al., Microbial Type III Polyketide Synthases, Comprehensive Natural Products II: Chemistry and Biology 2010, 1(5): 147-170.
Leicher, et al., Coexpression of the KCNA3B Gene Product with Kv1.5 Leads to a Novel A-type Potassium Channel, J. Biol. Chem. 1998, 273(52):35095-35101.
Liu, L. et al., Surveying the lipogenesis landscape in Yarrowia lipolytica through understanding the function of a Mga2p regulatory protein mutant, Metabolic Engineering (2015) 31:102-111.
Lussier, et al., Engineering microbes for plant polyketide biosynthesis, Computational and Structural Biotechnology Journal vol. 3, Issue 4, Oct. 2014, 1-11.

(Continued)

*Primary Examiner* — Marsha Tsay
(74) *Attorney, Agent, or Firm* — Meunier Carlin & Curfman LLC

(57) ABSTRACT

This invention relates to compositions and methods for the production of Type III polyketides using genetically modified oleaginous yeast strains, for example, *Yarrowia lipolytica*.

26 Claims, 9 Drawing Sheets

(56) References Cited

OTHER PUBLICATIONS

Madzak, C. et al., Strong hybrid promoters and integrative expression/secretion vectors for quasi-constitutive expression of heterologous proteins in the yeast Yarrowia lipolytica., J Mol Microbiol Biotechnol. Apr. 2000;2(2):207-16.
Melnikov et al., Random mutagenesis by recombinational capture of PCR products in Bacillus subtilis and Acinetobacter calcoaceticus, Nucleic Acids Research 1999, 27(4):1056-1062.
Okada, et al., Cloning and Analysis of Valerophenone Synthase Gene Expressed Specifically in Lupulin Gland of Hop (*Humulus lupulus* L.) Bioscience, Biotechnology, and Biochemistry, vol. 65, 2001—Issue 1, 150-155.
Saunders, et al., Triacetic acid lactone production in industrial *Saccharomyces* yeast strains, Journal of Industrial Microbiology & Biotechnology, May 2015, vol. 42, Issue 5, pp. 711-721.
Yu, et al., Type III polyketide synthases in natural product biosynthesis, 2012 International Union of Biochemistry and Molecular Biology Life 64(4):285-95.
International Preliminary Report on Patentability issued for Application No. PCT/US2017/022252, dated Sep. 27, 2018.
International Search Report and Written Opinion issued for Application No. PCT/US2017/022252, dated May 26, 2017.
Luo, Xingyu et al.,Characterization of the Far Transcription Factor Family in Aspergillus flavus, G3: Genes, Genomes, Genetics, early publication Aug. 16, 2016, vol. 6, pp. 3269-3281.
Poopanitpan, Napapol et al., An ortholog of farA of Aspergillus nidulans is implicated in the transcriptional activation of genes involved in fatty acid utilization in the yeast Yarrowia lipolytica, Biochemical and Biophysical Research Communications, published Oct. 25, 2010, vol. 402, Issue 4, pp. 731-735.

\* cited by examiner

COMPOSITIONS AND METHODS FOR TYPE III POLYKETIDE PRODUCTION IN OLEAGINOUS YEAST SPECIES

CROSS-REFERENCE TO RELATED APPLICATIONS

This application is a national stage application filed under 35 U.S.C. § 371 of PCT/US2017/022252 filed Mar. 14, 2017, which claims the benefit of U.S. Provisional Patent Application Ser. No. 62/307,912 filed Mar. 14, 2016, the disclosures of which are expressly incorporated herein by reference.

FIELD

This invention relates to compositions and methods for the production of Type III polyketides using genetically modified oleaginous yeast strains, for example, *Yarrowia lipolytica*.

BACKGROUND

The growing demand for renewable chemicals and fuels has spurred great interest in the use of cells as biochemical factories. Among possible molecules, polyketides are an interesting class of secondary metabolites produced by microbes and plants with native roles in processes such as cellular defense and communication (Austin, M. B. and J. P. Noel. Natural Product Reports, 2002. 20(1): p. 79-110; Keatinge-Clay, A. T. Natural Product Reports, 2012. 29(10): p. 1050; Lim, Y., et al. Molecules, 2016. 21(6): p. 806; Yu, D., et al. IUBMB Life, 2012. 64(4): p. 285-295). Polyketides represent a large family of diverse compounds synthesized from 2 or more carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, megalomicin, narbomycin, oleandomycin, picromycin, rapamycin, spinocyn, and tylosin are examples of polyketide compounds. Given the difficulty in producing polyketide compounds by traditional chemical methodology, and the typically low production of polyketides in wild-type microorganisms, there has been considerable interest in finding improved or alternate means to produce polyketide compounds.

While many polyketides can serve as potent antibiotics, this class of molecules also encompasses chemicals with other useful properties such as pigments, antioxidants, antifungals, and other bioactive traits. However, more unique, non-medical applications using these molecules have been limited in part due to their low abundance in native hosts. Specifically, polyketide producing organisms are typically unusual plants and bacteria that are not well suited for high level industrial production (Robinson, J. A. Philosophical Transactions of the Royal Society B: Biological Sciences, 1991. 332(1263): p. 107-114). Likewise, traditional chemical synthesis of polyketides is limited by low concentrations and challenging chiral centers. While the scale and price-point for pharmaceuticals can tolerate plant-based sourcing of polyketides, this is not an option for many larger-scale chemistry applications. For example, the simple polyketide triacetic acid lactone (TAL) has been proposed as a biorenewable platform chemical because it can be converted into a variety of valuable intermediates and products traditionally derived from fossil fuels (Chia, M., et al. Green Chemistry, 2012. 14(7): p. 1850). In one such application, TAL can be used as a feedstock for renewable sorbic acid production, a molecule with an annual global market of 100,000 tons. However, assuming current concentration in native plants (like *gerbera* daisies), it would be necessary to utilize 4-times the quantity of global arable land to produce enough TAL simply to satisfy the worlds' annual sorbic acid needs. As a result, applications of polyketides for unique chemical applications including polymers, coatings, and even commodity chemical production have not been explored or considered despite the chemical promise of these molecules.

Despite the chemical diversity inherent in polyketides, all of these molecules are built from the same common building blocks: acyl-CoA precursors (Austin, M. B. and J. P. Noel. Natural Product Reports, 2002. 20(1): p. 79-110; Keatinge-Clay, A. T. Natural Product Reports, 2012. 29(10): p. 1050; Lim, Y., et al. Molecules, 2016. 21(6): p. 806; Yu, D., et al. IUBMB Life, 2012. 64(4): p. 285-295). The enzymes that produce them, polyketide synthases (PKSs), catalyze a series of decarboxylative condensations to produce a polyketide chain and utilize intramolecular reactions within the chain to create cyclic compounds (Austin, M. B. and J. P. Noel. Natural Product Reports, 2002. 20(1): p. 79-110).

In one particular class of PKSs, the Type III PKS system enzymes consist of a small homodimer containing one active site where both chain extension and cyclization take place (Austin, M. B. and J. P. Noel. Natural Product Reports, 2002. 20(1): p. 79-110; Lim, Y., et al. Molecules, 2016. 21(6): p. 806; Yu, D., et al. IUBMB Life, 2012. 64(4): p. 285-295). Type III PKSs are able to produce a wide diversity of polyketide products by using a variety of larger, CoA-containing precursors as a starting unit. These starters range from small aliphatic molecules, such as acetyl-CoA, to larger ring-containing compounds derived from the phenylpropanoid pathway, such as 4-coumaroyl-CoA. Often, these CoA molecules are formed through the function of acid CoA ligases that convert carboxylic acids into corresponding CoA molecules.

Type III polyketides can be used as both bioactive molecules as well as monomeric precursors for polymer production. However, this application is limited by the availability of a production host suitable to produce these products at high yields to enable industrial-level production. For example, some Type III polyketides (i.e., triacetic acid lactone (TAL)), have been produced in industrial *Saccharomyces* yeast strains (Saunders, L. et al., J. Ind. Microbiol Biotechnol (2015) 42: 711-721). However, the yield for TAL from these strains was not sufficient for industrial-scale production of Type III polyketides, indicating the need for further metabolic and genetic engineering to achieve sufficient production levels.

Thus, there is a need for improved compositions and methods for producing higher yields of Type III polyketides.

SUMMARY

Disclosed herein are genetically modified oleaginous yeast strains and methods for the production of Type III polyketides at levels sufficient to enable industrial-scale production. Oleaginous yeast species, such as *Yarrowia lipolytica*, are excellent hosts for the production of Type III polyketides due to their already abundant precursor pools of CoA molecules. Through metabolic engineering, the flux of these organisms can be shifted from the production of fatty acids to the production of Type III polyketides. The invention disclosed herein thus serves as an enabling technology to allow polyketides to be used as chemical feedstocks for a variety of new applications in the chemical and material science industries.

In one aspect, provided herein is a genetically modified oleaginous yeast cell comprising a heterologous gene, wherein the heterologous gene encodes a Type III polyketide synthase. In one embodiment, the oleaginous yeast cell is *Yarrowia lipolytica*.

In one embodiment, provided herein is a genetically modified oleaginous yeast cell comprising a heterologous gene, wherein the heterologous gene is selected from the group consisting of the CAA86219.2 (g2ps1) gene from *Gerbera hybrida*, AY517486 (ALS) gene from *Rheum palmatum*, JX840717-JX840724 (PHLD) gene from *Pseudomonas fluorescens*, B0LDU5 gene from *Rubus idaeus*, B1VLQ8 (RPPA) gene from *Streptomyces griseus*, SCO1206 (THNS) from *Streptomyces coelicolor*, BAB12102.2 gene from *Humulus lupulus*, or a combination thereof. In one embodiment, the heterologous gene is the CAA86219.2 (g2ps 1; 2-pyrone synthase) gene from *Gerbera hybrida*.

The genetically modified yeast strains disclosed herein can be used for the increased production of Type III polyketides. In one aspect, disclosed herein is a method for the production of a Type III polyketide comprising: 1) culturing an oleaginous yeast cell in a growth medium, wherein the yeast cell comprises a heterologous gene, wherein the heterologous gene encodes a Type III polyketide synthase; and 2) isolating said Type III polyketide.

Disclosed herein is a method for the production of a Type III polyketide comprising: 1) culturing an oleaginous yeast cell in a growth medium, wherein the yeast cell comprises a heterologous gene, wherein the heterologous gene is selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, and BAB12102.2 gene from *Humulus lupulus*; and 2) isolating said Type III polyketide.

In another embodiment, disclosed herein is a method for the production of a Type III polyketide comprising: 1) culturing a *Yarrowia lipolytica* yeast cell in a growth medium, wherein the yeast cell comprises one or more heterologous genes selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, and BAB12102.2 gene from *Humulus lupulus*; and 2) isolating said Type III polyketide.

In one embodiment, the heterologous gene is integrated into the genome of the yeast cell. In another embodiment, at least two copies of the heterologous gene are present in the genome of the yeast cell. In one embodiment, the heterologous gene is incorporated into a gene expression cassette comprising a promoter and the heterologous gene, wherein the gene expression cassette is integrated into the genome of the yeast cell. In an alternative embodiment, the heterologous gene is episomally expressed from a plasmid.

In another aspect, the genetically modified oleaginous yeast cell (e.g., *Yarrowia lipolytica*) comprises an additional genetic modification. For example, the additional genetic modification can increase the acetyl-CoA and/or malonyl-CoA levels or fluxes. In some embodiments, the additional genetic modification increases the rate of beta-oxidation to increase the acetyl-CoA or malonyl-CoA levels or fluxes.

In some embodiments, the additional genetic modification comprises the elimination or the reduction of *Yarrowia lipolytica* gene phosphatidate phosphatase (PAH1; YALI0D27016); and/or the additional genetic modification comprises the overexpression of one or more *Yarrowia lipolytica* genes selected from the group consisting of peroxin 10 (PEX10; YALI0001023), multifunctional β oxidation protein (oxidoreductase and hydro-lyase) (MFE1; YALI0E15378), primary oleate regulator (POR1; YALI0D12628), or a combination thereof.

In some embodiments, the additional genetic modification comprises: 1) the elimination or the reduction of one or more *Yarrowia lipolytica* genes selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof; and/or 2) the overexpression of one or more *Yarrowia lipolytica* genes selected from the group consisting of Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793g), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0003025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydrolyase) (MFE1; YALI0E15378), primary oleate regulator (POR1; YALI0D12628), or a combination thereof.

In one embodiment, the additional genetic modification is overexpression of Pyruvate Decarboxylase (Pyrudecarb (PDC1); YALI0D10131p). In one embodiment, the additional genetic modification is overexpression of Malate Dehydrogenase (MAE1; YALI0E18634p). In one embodiment, the additional genetic modification is overexpression of ATP-Citrate Lyase Subunit 1 (ACL1; YALI0E34793p). In one embodiment, the additional genetic modification is overexpression of ATP-Citrate Lyase Subunit 2 (ACL2; YALI0D24431p). In one embodiment, the additional genetic modification is overexpression of Pyruvate Dehydrogenase E1 Component Subunit Alpha (PDC-E1; YALI0F20702p). In one embodiment, the additional genetic modification is overexpression of Acetyl-CoA Carboxylase (AceCarb (ACC1); YALI0C11407g). In one embodiment, the additional genetic modification is overexpression of Acetyl-CoA Synthetase (AceCoA; YALI0F05962g).

In one embodiment, the *Yarrowia lipolytica* yeast cell is a wild-type strain. In a further embodiment, the wild-type strain is a PO1f strain. In an additional embodiment, the *Yarrowia lipolytica* yeast cell has been preoptimized for lipid overproduction. In one embodiment, the yeast cell is an L36 strain.

In some embodiments, the growth medium comprises a majority carbon source selected from the group consisting of glucose, glycerol, xylose, fructose, mannose, ribose, sucrose, and lignocellulosic biomass. In one embodiment, the growth medium comprises glucose as the majority carbon source. In an additional embodiment, the growth medium comprises a secondary carbon source selected from lignin or lignin derived aromatic compounds.

In some embodiments, the method further comprises the addition of a solubility agent, wherein the solubility agent increases the solubility of the Type III polyketide. In one embodiment, the solubility agent is triethylene glycol. In one embodiment, the solubility agent is gamma valerolactone.

BRIEF DESCRIPTION OF THE DRAWINGS

The accompanying figures, which are incorporated in and constitute a part of this specification, illustrate several aspects described below.

DETAILED DESCRIPTION

Figure 1:
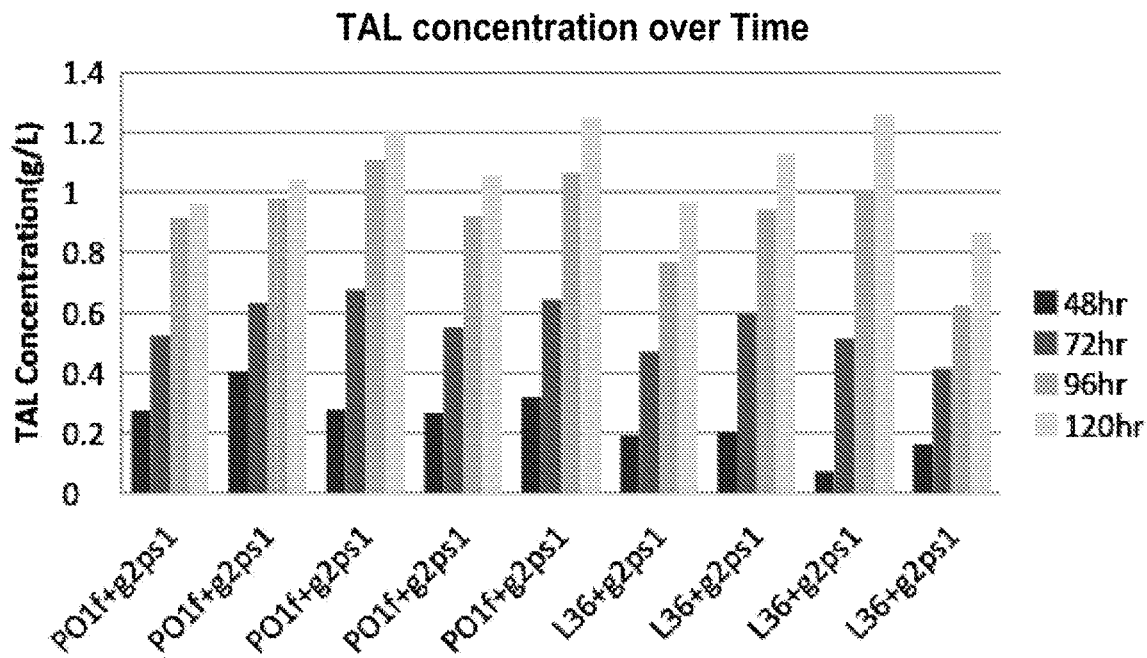
FIG. 1. Triacetic acid lactone (TAL) production over time in wild type (PO1f) *Y. lipolytica* and a previously engineered *Y. lipolytica* strain for high lipid production (L36).

Disclosed herein are compositions and methods for production of high levels of Type III polyketides using oleaginous yeast strains, for example, a genetically engineered fungal host, *Yarrowia lipolytica*. While production has been demonstrated in other hosts, titers and yields remain too low for utility in an industrial setting. The engineered fungal hosts disclosed herein can have production levels that exceed previous reported production of these Type III polyketide molecules. The particular features of the engineered oleaginous yeast strains, for example, *Yarrowia lipolytica* strains, include the ability to produce extremely high levels (g/L levels) in these cells. These levels of production can enable industrial scale production for the first time for these types of molecules.

The genetically modified yeast strains and methods disclosed herein create a renewable, clean method for the production of Type III polyketides in microorganisms. Previous methods for obtaining these molecules include extracting them from plants and hard to cultivate organisms. Based on these prior methods, quantities of polyketides have been generally too low for practical use as commodity and/or bulk chemicals. Compared to these prior approaches (hard to use organisms and plant extractions), the present disclosure allows very rapid production of high titers (g/L values) at yields that exceed previously reported recombinant organisms. These higher titers of polyketides can be used as commodity chemicals and monomers for new materials.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

The term "oleaginous organism" means an organism (e.g. a cell such as a yeast cell) that is capable of producing a lipid, lipid precursor, oleochemical, or oil (or combinations thereof) at a level exceeding the amount required for normal cellular survival and propagation of the organism (e.g. cell, yeast cell), such as for example necessary for structural integrity (e.g. membrane formation and maintenance) and cellular maintenance. Examples of amounts exceeding the amount required for normal cellular survival and propagation include an amount of lipids, oils, lipid precursors, and oleochemicals greater than 20% wt/wt total dry weight. In some embodiments, the oleaginous organism is an oleaginous yeast. In some embodiments, the oleaginous yeast is from a genus selected from the group consisting of *Apiotrichum, Candida, Cryptococcus*, Debaromyces, *Endomycopsis, Geotrichum, Hyphopichia, Lipomyces*, Lypomyces, *Pichia, Rodosporidium, Rhodotorula*, Sporobolomyces, Starmerella, *Torulaspora, Trichosporon, Wickerhamomyces, Yarrowia*, and Zygoascus. In embodiments, the oleaginous yeast is selected from the group consisting of *Apiotrichum* curvatura, *Candida* apicola, *Candida curvata, Candida revkaufi, Candida pulcherrima, Candida tropicalis, Candida utilis, Cryptococcus curvatus, Cryptococcus* terricolus, Debaromyces *hansenii, Endomycopsis vernalis, Geotrichum carabidarum, Geotrichum cucujoidarum, Geotrichum histeridarum, Geotrichum silvicola, Geotrichum vulgare, Hyphopichia burtonii, Lipomyces* lipoferus, *Lipomyces* lipofer, Lypomyces orentalis, *Lipomyces* starkeyi, *Lipomyces* tetrasporous, *Pichia mexicana, Rodosporidium sphaerocarpum, Rhodosporidium toruloides, Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis, Rhodotorula minuta, Rhodotorula mucilaginosa, Rhodotorula mucilaginosa Rhodotorula mucilaginosa, Rhodotorula terpenoidalis, Rhodotorula* toruloides, Sporobolomyces alborubescens, Starmerella *bombicola, Torulaspora delbruekii, Torulaspora pretoriensis, Trichosporon behrend, Trichosporon brassicae, Trichosporon cutaneum, Trichosporon domesticum, Trichosporon fermentans, Trichosporon laibachii, Trichosporon loubieri, Trichosporon* loubieri var. loubieri, *Trichosporon* montevideense, *Trichosporon pullulans, Wickerhamomyces canadensis, Yarrowia lipolytica*, and Zygoascus meyerae.

The term "carbon substrate" means a carbon source that a microorganism (e.g. oleaginous yeast) will metabolize to derive energy (e.g. monosaccharides, oligosaccharides, polysaccharides, alkanes, fatty acids, esters of fatty acids, monoglycerides, acetate, carbon dioxide, methanol, formaldehyde, formate or carbon-containing amines). The term "carbon source" refers to a carbon containing composition (e.g. compound, mixture of compounds) that an organism (e.g. oleaginous organism, yeast cell) may metabolize for use by the organism or that may be used for organism viability. A "majority carbon source" refers to a carbon containing composition that accounts for greater than 50% of the available carbon sources for an organism (e.g. in a media, in a growth media, in a defined media for growing yeast cells, or in a defined media for producing lipids by yeast cells) at a specified time (e.g. media when starting a yeast culture, media in a bioreactor when growing yeast, or media when producing lipids from yeast). In embodiments, an oleaginous yeast may be cultured using a medium comprising a majority carbon source selected from the group consisting of glucose, glycerol, xylose, fructose, mannose, ribose, sucrose, and lignocellusic biomass. In embodiments, an oleaginous yeast may be cultured using a medium comprising one or more carbon sources selected from the group consisting of glucose, fructose, sucrose, lactose, galactose, xylose, mannose, rhamnose, arabinose, glycerol, acetate, depolymerized sugar beet pulp, black liquor, corn starch, depolymerized cellulosic material, corn stover, sugar beet pulp, switchgrass, milk whey, molasses, potato, rice, sorghum, sugar cane, wheat, and mixtures thereof (e.g. mixtures of glycerol and glucose, mixtures of glucose and xylose, mixtures of fructose and glucose, mixtures of sucrose and depolymerized sugar beet pulp, black liquor, corn starch, depolymerized cellulosic material, corn stover, sugar beet pulp, switchgrass, milk whey, molasses, potato, rice, sorghum, sugar cane, and/or wheat). In some embodiments, an oleaginous yeast is cultured using a medium comprising one or more carbon sources selected from the group consisting of depolymerized sugar beet pulp, black liquor, corn starch, depolymerized cellulosic material, corn stover, sugar beet pulp, switchgrass, milk whey, molasses, potato, rice, sorghum, sugar cane, thick cane juice, sugar beet juice, and wheat. In embodiments, an oleaginous yeast is cultured using a medium comprising lignocellulosic biomass. In embodiments carbon sources may be monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, or barley malt). Additionally, carbon sources may include alkanes, fatty acids, esters of fatty acids, monoglycerides, diglycerides, triglycerides, phospholipids, various commercial sources of fatty acids including vegetable oils (e.g., soybean oil) or animal fats. In some embodiments, the culture medium may contain, in addition to the primary (or majority) carbon source, one or more secondary carbon sources. In some embodiments, the secondary carbon source comprises lignin or lignin derived aromatic compounds. In some embodiments, the secondary carbon source comprises lignin breakdown products. In some embodiments, the lignin breakdown products include, for example, paracoumaryl, coniferyl and sinapyl acids. In some embodiments, the secondary carbon source can include lignan derived compounds including secoisolariciresinol, matairesinol, lariciresinol, and pinoresinol. In some embodiments, the secondary carbon source may be an acid including, for example, p-coumaric acid, trans-ferulic acid, 3-phenylpropanoic acid, octanoic acid, trans-cinnamic acid, 3-fluorocinnamic acid, benzoic acid, 3-aminobenzoic acid, propanoic acid, 2-bromobenzoic acid, phenylacetic acid, phenylpyruvic acid, pentanoic acid, methylmalonic acid, ethylmalonic acid, chloromalonic acid, cinamic acid, and other aliphatic acids.

Nitrogen may be supplied from an inorganic (e.g., $(NH_4)_2SO_4$) or organic source (e.g., urea, glutamate). The term "nitrogen source" refers to a nitrogen containing composition (e.g. compound, mixture of compounds, salt) that an organism (e.g. oleaginous organism, yeast cell) may metabolize for use by the organism or that may be used for organism viability. A "majority nitrogen source" refers to a nitrogen containing composition that accounts for greater than 50% of the available nitrogen sources for an organism (e.g. in a media, in a growth media, in a defined media for growing yeast cells, or in a defined media for producing lipids by yeast cells) at a specified time (e.g. media when starting a yeast culture, media in a bioreactor when growing yeast, or media when producing lipids from yeast).

The term "biomass" refers to material produced by growth and/or propagation of cells. "Lignocellulosic biomass" is used according to it plain and ordinary meaning and refers to plant dry matter comprising carbohydrate (e.g. cellulose or hemicellulose) and polymer (e.g. lignin). Lignocellulosic biomass may include agricultural residues (e.g. corn stover or sugarcane bagasse), energy crops (e.g. poplar trees, willow, *Miscanthus purpureum, Pennisetum purpureum*, elephant grass, maize, Sudan grass, millet, white sweet clover, rapeseed, giant *miscanthus*, switchgrass, jatropha, *Miscanthus giganteus*, or sugarcane), wood residues (e.g. sawmill or papermill discard), or municipal paper waste.

The term "culture", "cultivate", and "ferment" are used interchangeably and refer to the intentional growth, propagation, proliferation, and/or enablement of metabolism, catabolism, and/or anabolism of one or more cells (e.g. oleaginous yeast). The combination of both growth and propagation may be termed proliferation. Examples include production by an organism of a polyketide of interest. Culture does not refer to the growth or propagation of microorganisms in nature or otherwise without human intervention.

The term "growth" means an increase in cell size, total cellular contents, and/or cell mass or weight of a cell (e.g. oleaginous yeast).

A "growth media" or "growth medium" as used herein can be a solid, powder, or liquid mixture which comprises all or substantially all of the nutrients necessary to support the growth of yeasts; various nutrient compositions are preferably prepared when particular yeast species are being assayed. Amino acids, carbohydrates, minerals, vitamins and other elements known to those skilled in the art to be necessary for the growth of yeasts are provided in the medium. In one embodiment, the growth medium is liquid. In one embodiment, the growth medium is a production medium (for example, medium optionally containing higher concentrations of glucose and/or altered concentrations of nitrogen) used for the large scale production of Type III polyketides from oleaginous yeast cells.

The term "lipid" refers to a class of molecules that are soluble in nonpolar solvents (e.g. ether or chloroform), are relatively or completely insoluble in water, and include one or more hydrocarbon chains which are hydrophobic. In embodiments, a lipid may be a triacylglyeride (i.e. fat), fatty acid (e.g. saturated or unsaturated); glyceride or glycerolipid (e.g. monoglyceride, diglyceride, triglyceride, neutral fat, phosphoglyceride, or glycerophospholipid); sphingolipid; sterol lipid (e.g. cholesterol or a steroid hormone); prenol lipid (e.g. terpenoid); fatty alcohol; wax; polyketide; sugar-linked lipid, glycolipid, or protein-linked lipid.

The term "oil" means a triacylglyceride (or triglyceride oil), produced by an organism (e.g. oleaginous organism, oleaginous yeast, plant, and/or animal). An oil is generally liquid at normal ambient temperatures and pressures. In embodiments, oil may be vegetable or seed oils derived from plants (e.g. soy, rapeseed, canola, palm, palm kernel, coconut, corn, olive, sunflower, cotton seed, *cuphea*, peanut, camelina *sativa*, mustard seed, cashew nut, oats, lupine, kenaf, calendula, hemp, coffee, linseed, hazelnut, *euphorbia*, pumpkin seed, coriander, *camellia*, sesame, safflower, rice, tung oil tree, cocoa, copra, pium poppy, castor beans, pecan, jojoba, jatropha, macadamia, Brazil nuts, avocado, or combinations thereof). An oil may include a plurality of different triacylglycerides. For example, a vegetable or seed oil may include more than one triacylglyceride and use of the name of that vegetable or seed oil (e.g. soy, rapeseed, canola, palm, etc.) when referring to an oil generated by an oleaginous organism will be understood to mean an oil including most (e.g. all) of the triacylglycerides normally in the vegetable or seed oil (e.g. at different ratios relative to each other or the same or similar ratios relative to each other). In other embodiments, an oil may be a plurality of triacylglyceride and other lipid molecules produced by an oleaginous organism.

The term "propagation" refers to an increase in cell number via cell division.

The term "promoter" or "regulatory element" refers to a region or sequence determinants located upstream or downstream from the start of transcription and which are involved in recognition and binding of RNA polymerase and other proteins to initiate transcription. Promoters need not be of yeast origin, for example, promoters derived from viruses or from other organisms can be used in the compositions or methods described herein.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e., a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., Molecular Cloning A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). In embodiments, a recombinant nucleic acid is a nucleic acid in an oleaginous organism (e.g. oleaginous yeast) that has been manipulated by a human, for example a recombinant nucleic acid comprising a coding region for a protein that is overexpressed in an oleaginous organism relative to the absence of the recombinant nucleic acid or a recombinant nucleic acid that results in disruption of a coding region or promoter region of an oleaginous organism and reduces or eliminates expression of a protein relative the absence of the recombinant nucleic acid. One of skill will recognize that nucleic acids (e.g. polynucleotides) can be manipulated in many ways and are not limited to the examples above. "Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones. The term encompasses nucleic acids containing known analogues of natural nucleotides which have similar or improved binding properties, for the purposes desired, as the reference nucleic acid. A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., Molecular Cloning A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%,94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) J Mol. Biol. 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0)

and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism. For example, the sequence of a heterologous gene expressed in *Yarrowia lipolytica* may be "codon optimized" to optimize gene expression based on the preferred codon usage in *Yarrowia lipolytica*.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al. One of skill will recognize that these values can be appropriately adjusted to determine corresponding identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

The term "modulator" refers to a composition that increases or decreases the level of a target molecule or the level of activity or function of a target molecule or the physical state of the target of the molecule. In embodiments a modulator is a recombinant nucleic acid that is capable of increasing or decreasing the amount of a protein in a cell or the level of activity of a protein in a cell or transcription of a second nucleic acid in a cell. In embodiments, a modulator increases or decreases the level of activity of a protein or the amount of the protein in a cell. The term "modulate" is used in accordance with its plain and ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, a recombinant nucleic acid that modulates the level of activity of a protein may increase the activity or amount of the protein relative the absence of the recombinant nucleic acid. In embodiments, an increase in the activity or amount of a protein may include overexpression of the protein. "Overexpression" is used in accordance with its plain and ordinary meaning and refers to an increased level of expression of a protein relative to a control (e.g. cell or expression system not including a recombinant nucleic acid that contributes to the overexpression of a protein). In embodiments, a decrease in the activity or amount of a protein may include a mutation (e.g. point mutant, loss of function mutation, missense mutation, deletion, or insertion of heterologous nucleic acid; all/any of which may be in the coding region for a protein or in an operably linked region (e.g. promoter)) of the protein. The term "increased" refers to a detectable increase compared to a control.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a host organism (e.g. oleaginous yeast). In embodiments, the nucleic acid molecule may be a plasmid that replicates autonomously or it may integrate into the genome of the host organism (e.g. oleaginous yeast). Host organisms containing the transformed nucleic acid molecule may be referred to as "transgenic" or "recombinant" or "transformed" organisms (e.g. oleaginous yeast). A "genetically modified" organism (e.g. genetically modified yeast cell) is an organism (e.g. yeast cell) that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids. Genetically modified organisms may be made by rational modification of a nucleic acid or may be made by use of a mutagen or mutagenesis protocol that results in a mutation that was not identified (e.g. intended or targeted) prior to the use of the mutagen or mutagenesis protocol (e.g. UV exposure, EMS exposure, mutagen exposure, random genomic mutagenesis, transformation of a library of different nucleic acid constructs). Genetically modified organisms that include a modification (e.g. modification, insertion, deletion, mutation) not previously known or intended prior to making of the genetically modified organism may be identified through screening a plurality of organism including one or more genetically modified organisms by using a selection criteria that identifies the genetically modified organism of interest (e.g. an increased level of lipids, lipid precursors, and/or oleochemicals; floats above an organism not including the same genetic modification). In embodiments, a genetically modified organism includes a recombinant nucleic acid.

As used herein, the term "episome" or "episomally" is intended to refer to an extrachromosomal DNA moiety or plasmid that can replicate autonomously in a host cell when physically separated from the chromosomal DNA of the host cell.

Methods for synthesizing sequences and bringing sequences together are well established and known to those of skill in the art. For example, in vitro mutagenesis and selection, site-directed mutagenesis, error prone PCR (Melnikov et al., Nucleic Acids Research, 27(4):1056-1062 (Feb. 15, 1999)), "gene shuffling" or other means can be employed to obtain mutations of naturally occurring genes.

The term "wild-type" as used herein when referring to an oleaginous organism (e.g. yeast strain or *Yarrowia lipolytica* strain) means an organism that has not been genetically modified to improve production of a lipid (e.g. increase yield of a lipid, alter the structure of a lipid produced by the organism, reduce production of one lipid to improve production of a second lipid, or modulate the production of a lipid). In some embodiments, a wild-type yeast strain may be auxotrophic for one or more compounds (e.g. leucine and/or uracil). In one embodiment, a wild-type strain of *Yarrowia lipolytica* is selected for use in the methods herein. In one embodiment, a wild-type *Yarrowia lipolytica* strain is PO1f (ATCC #MYA-2613), a leucine and uracil auxotroph devoid of any secreted protease activity (Madzak, C. et al., J Mol Microbiol Biotechnol. 2000 April; 2(2):207-16). In one embodiment, a wild-type *Yarrowia lipolytica* strain is L36, a leucine and uracil auxotroph devoid of any secreted protease activity (Liu, L. et al., Metabolic Engineering (2015) 31:102-111).

The term "oleochemical" is used herein in accordance with its well-known meaning and refers to chemicals or compounds derived from lipids or fats. In embodiments, an oleochemical is a lipid or fat derived from a different lipid or fat. In embodiments an oleochemical is a chemical or compound produced by an oleaginous organism. In embodiments, an oleochemical is a chemical or compound derived from a lipid or lipid precursor produced by an oleaginous organism (e.g., fatty acid esters such as methyl esters, ethyl esters, propyl esters, or butyl esters that are derived from a fatty acid produced by an oleaginous organism by transesterification). In embodiments, an oleochemical may include further in vivo or in vitro modification of a lipid or lipid precursor enabled by endogenous or heterologous modifying enzymes or chemical reactions.

The term "lipid precursor" is used in accordance with its well-known meaning and refers to a pathway intermediate (e.g., acetyl-CoA or malonyl-CoA) in the biosynthesis of a lipid. In embodiments, a lipid precursor may be any molecule along the biosynthetic pathway making triglycerides including free citrate, acetyl-CoA, free fatty acids, pyruvate, citric acid cycle intermediates, diacylglycerides, and/or triacylglycerides.

Type III Polyketide Synthases

Polyketide synthases (PKS) are multifunctional enzymes related to fatty acid synthases (FASs). PKS catalyze the biosynthesis of polyketides through repeated (decarboxylative) condensations between acylthioesters, usually acetyl, propionyl, malonyl or methylmalonyl.

Three general classes of polyketide synthases (PKS) exist. One class, known as Type I, "complex" or "modular" PKS, is represented by the PKS for macrolides such as erythromycin. The "modular" PKS are assemblies of several large multifunctional proteins carrying, between them, a set of separate active sites for each step of carbon chain assembly and modification. Structural diversity occurs in this class from variations in the number and type of active sites in the PKS.

The second class of PKS, called Type II or "aromatic" PKS, is represented by the synthases for aromatic compounds. The "aromatic" PKS are typically encoded by at least three separate open reading frames and have a single set of iteratively used active sites.

A third class of PKS is generally known as "fungal" PKS and is typically a multifunctional protein encoded in a single reading frame. The fungal PKS thus do not fit neatly into the categorization of aromatic versus modular and thus constitute a third group.

Type III polyketides have a myriad of uses such as nutritional supplements, bioactive compounds, pharmaceuticals, energetic materials, and as monomers for new types of polymeric materials. Examples of Type III polyketides include the active ingredient in aloe, naringenin, resveratrol, stilbenes, phloroglucinol, curcuminoids, and gingerol.

Examples of Type III polyketides that can be produced using the genetically modified yeast strains disclosed herein include, but are not limited to, triacetic acid lactone, aloesone, phloroglucinol, benzalacetone, 1,8-Dihydroxynaphthalene, flaviolin and phloroisovalerophenone.

Triacetic acid lactone can be made by expressing a triacetic acid lactone synthase (CAA86219.2; g2ps1 gene) from *Gerbera hybrida*. Aloesone can be made by expressing an aloesone synthase (AY517486) from *Rheum palmatum*. Phloroglucinol can be made by expressing the JX840717-JX840724 genes from *Pseudomonas fluorescens*. Benzalacetone can be made by expressing the B0LDU5 from *Rubus idaeus*. 1,8-Dihydroxynaphthalene and flaviolin can be made by expressing the B1VLQ8 gene from *Streptomyces griseus*. 1,8-Dihydroxynaphthalene can be made by expressing the SCO1206 from *Streptomyces coelicolor*. Finally, phloroisovalerophenone can be made by expressing the BAB12102.2 gene from *Humulus lupulus*.

Triacetic acid lactone (TAL) can be made by expressing a triacetic acid lactone synthase (CAA86219.2; g2ps1; 2-pyrone synthase gene) from *Gerbera hybrida*. Like other Type III polyketide synthases, g2ps1 is a relatively small protein that uses a single active site for decarboxylation and cyclization reactions. 2-PS utilizes acetyl coezyme A (acetyl CoA) as an initial substrate and catalyzes the decarboxylation and condensation of two malonyl-CoAs to produce TAL.

Phloroglucinol (1,3,5-trihydroxybenzene) and its derivatives are widely used in commerce. Phloroglucinol and its derivatives, for example, trimethylphloroglucinol, are used as pharmaceutical agents, for example, as antispasmodics. Phloroglucinol is used as a starting material or intermediate in pharmaceutical, microbicide, and other organic syntheses. Phloroglucinol is used as a stain for microscopy samples that contain lignin (e.g., wood samples), and it is used in the manufacture of dyes, including leather, textile, and hair dyes. It is used in the manufacture of adhesives and as an epoxy resin curing agent, and in the preparation of explosives. Phloroglucinol also functions as an antioxidant, stabilizer, and corrosion resistance agent, and is utilized as a coupling agent for photosensitive duplicating paper, as a substitute for silver iodide in rain-making, as a bone sample decalcifying agent, and as a floral preservative.

Furthermore, numerous polyketide products can be made from malonyl-coA precursors in combination with acetyl-coA precursors. As acetyl-coA is a precursor of malonyl-coA, no additional modifications to a malonyl-coA producing strain are needed. Products can be made by expressing enzyme functions to convert malonyl-coA in addition to acetyl-coA into products. Any of the strains discussed in the specification that increase flux through malonyl-coA can be used to produce these products. 6-hydroxymellein can be made by expressing a 6-hydroxymellein synthase from either Aloe or *Daucus carota*.

Aloesone can be made by expressing an aloesone synthase from either Moe *arborescens* or *Rheum palmatum*. Benzalacetone can be made by expressing the B0LDU5 from *Rubus idaeus*. The B0LDU5 enzyme is a plant-specific type III polyketide synthase of the chalcone synthase (CHS) superfamily. Phloroisovalerophenone can be made by expressing the BAB12102.2 gene from *Humulus lupulus*. 1,8-Dihydroxynaphthalene and flaviolin (4,5,7-trihydroxynaphthalene-1,2-dione) can be made by expressing the B1VLQ8 gene from *Streptomyces griseus*. 1,8-Dihydroxynaphthalene can be made by expressing the SC01206 gene from *Streptomyces coelicolor*. The BAB12102.2 gene encodes phloroisovalerophenone synthase and produces 3-methyl-1-(2,4,6-trihydroxyphenyl)butan-1-one (phloroisovalerophenone).

In some embodiments, the heterologous gene sequence or gene sequence encoding a Type III polyketide synthase may be codon optimized, without changing the resulting polypeptide sequence. In some embodiments, the codon optimization includes replacing at least one, or more than one, or a significant number, of codons with one or more codons that are more frequently used in the genes of that selected oleaginous yeast. For example, the sequence of a heterologous gene expressed in *Yarrowia lipolytica* may "codon optimized" to optimize gene expression based on the preferred codon usage in *Yarrowia lipolytica*.

In some embodiments, the heterologous gene is substantially identical to the wild-type sequence for the heterologous gene in its native host species. In some embodiments, the heterologous gene is about 60% identical, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%,94%, 95%, 96%, 97%, 98%, 99% or higher, over a specified region when compared and aligned for maximum correspondence with the wild-type sequence for the heterologous gene in its native host species.

Oleaginous Yeasts

In some embodiments, the oleaginous organism is an oleaginous yeast. In some embodiments, the oleaginous yeast is from a genus selected from the group consisting of Apiotrichum, *Candida, Cryptococcus*, Debaromyces, *Endomycopsis, Geotrichum, Hyphopichia, Lipomyces*, Lypomyces, *Pichia, Rodosporidium, Rhodotorula*, Sporobolomyces, Starmerella, *Torulaspora, Trichosporon, Wickerhamomyces, Yarrowia*, and Zygoascus. In embodiments, the oleaginous yeast is selected from the group consisting ofApiotrichum curvatum, *Candida* apicola, *Candida curvata, Candida revkaufi, Candida pulcherrima, Candida tropicalis, Candida utilis, Cryptococcus curvatus, Crypto-* coccus terricolus, Debaromyces *hansenii, Endomycopsis vernalis, Geotrichum carabidarum, Geotrichum cucujoidarum, Geotrichum histeridarum, Geotrichum silvicola, Geotrichum vulgare, Hyphopichia burtonii, Lipomyces* lipoferus, *Lipomyces* lipofer, Lypomyces orentalis, *Lipomyces* starkeyi, *Lipomyces* tetrasporous, *Pichia mexicana, Rodosporidium sphaerocarpum, Rhodosporidium toruloides, Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis, Rhodotorula minuta, Rhodotorula mucilaginosa, Rhodotorula mucilaginosa Rhodotorula mucilaginosa, Rhodotorula terpenoidalis, Rhodotorula* toruloides, Sporobolomyces alborubescens, Starmerella *bombicola, Torulaspora delbruekii, Torulaspora pretoriensis, Trichosporon behrend, Trichosporon brassicae, Trichosporon cutaneum, Trichosporon domesticum, Trichosporon fermentans, Trichosporon laibachii, Trichosporon loubieri, Trichosporon* loubieri var. loubieri, *Trichosporon* montevideense, *Trichosporon pullulans, Wickerhamomyces canadensis, Yarrowia lipolytica,* and Zygoascus meyerae.

In another embodiment, the yeast cell is selected from the group consisting of the genera *Yarrowia, Candida, Rhodotorula, Rhodosporidium, Cryptococcus, Trichosporon* and *Lipomyces*. In embodiments, the yeast cell is selected from the group consisting of *Rhodosporidium toruloides, Lipomyces* starkeyii, *Lipomyces* lipoferus, Apiotrichum curvatum, *Candida curvata, Cryptococcus curvatus, Trichosporon fermentans, Candida* revkaufi, *Candida pulcherrima, Candida tropicalis, Candida utilis, Trichosporon pullans, Trichosporon cutaneum, Rhodotorula glutinus, Rhodotorula graminis* and *Yarrowia lipolytica*. In embodiments, the yeast cell is selected from the group consisting of *Lipomyces* starkeyii, *Rhodosporidium toruloides*, Apiotrichum curvatum, *Candida curvata, Cryptococcus curvatus, Trichosporon fermentans, Rhodotorula glutinus,* and *Yarrowia lipolytica*.

In one embodiment, the yeast cell is *Yarrowia lipolytica*. *Yarrowia lipolytica*'s genetic tractability, efficient utilization of many energy sources, and native capacity to accumulate lipids make it an ideal platform for synthesis of Type III polyketides. *Y. lipolytica* has a fully defined metabolic engineering toolbox that enables intracellular flux control through genomic manipulation. *Y. lipolytica* is commonly utilized for heterologous protein excretion and to examine and manipulate lipid and fatty acid metabolism, and has proven amenable to downstream manipulation of its fatty acid content to alter desaturation levels or to synthesize novel oleo-chemicals. Thus, *Y. lipolytica* lipid reserves are ideal for in vivo catalysis to alkanes, fatty acid esters or for standard transesterification-based conversion and use as biodiesel. In particular, biodiesel production grants a high net energy gain compared to other alternative fuels with minimal environmental impact, and harvesting lipid reserves from a microbial source such as *Y. lipolytica* enables easily scaled-up production without compromising food supply. *Y. lipolytica*'s natural lipid content consists of predominantly C16:0, C16:1, C18:0, C18:1, and C18:2 fatty acids, very similar to the fatty acid content of biodiesel derived from soybeans and rapeseed. Economic viability can be greatly improved by fully utilizing all sugars from lignocellulosic biomass or by using carbon from industrial waste streams. In this regard, *Y. lipolytica* can efficiently utilize hydrophobic and waste carbon sources, such as crude glycerol, and has shown excellent heterologous gene expression when utilizing glucose, sucrose, glycerol, or oleic acid as a carbon source. Finally, *Y. lipolytica* is regarded as a "safe-to-use" organism. See additional discussion of *Y. lipolytica* in WO2014179748, which is hereby incorporated by reference.

Genetically-Modified Oleaginous Yeast Cells

Disclosed herein are genetically modified oleaginous yeast strains and methods for the production of Type III polyketides at levels sufficient to enable industrial-scale production. Oleaginous yeast species, such as *Yarrowia lipolytica*, are excellent hosts for the production of Type III polyketides due to their already abundant precursor pools of CoA molecules. Through metabolic engineering, the flux of these organisms can be shifted from the production of fatty acids to the production of Type III polyketides.

In one aspect, provided herein is a genetically modified oleaginous yeast cell comprising a heterologous gene, wherein the heterologous gene encodes a Type III polyketide synthase. In one embodiment, the oleaginous yeast cell is *Yarrowia lipolytica*.

In one embodiment, provided herein is a genetically modified oleaginous yeast cell comprising a heterologous gene, wherein the heterologous gene encodes a Type III polyketide synthase selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, BAB12102.2 gene from *Humulus lupulus*, or a combination thereof. In one embodiment, the heterologous gene is the CAA86219.2 (g2ps1; 2-pyrone synthase) gene from *Gerbera hybrida*.

In one aspect, provided herein is a genetically modified *Yarrowia lipolytica* yeast cell comprising a heterologous gene selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, BAB12102.2 gene from *Humulus lupulus*, or a combination thereof.

In one embodiment, the heterologous gene is integrated into the genome of the yeast cell. In another embodiment, at least two copies of the heterologous gene are present in the genome of the yeast cell. In one embodiment, the heterologous gene is incorporated into a gene expression cassette comprising a promoter and the heterologous gene, wherein the gene expression cassette is integrated into the genome of the yeast cell. In an alternative embodiment, the heterologous gene is episomally expressed from a plasmid.

Other genetic changes to the yeast strain can also help improve the production of the targeted Type III polyketide. In another aspect, the genetically modified *Yarrowia lipolytica* yeast cell (e.g. containing a heterologous gene comprises an additional genetic modification. For example, the additional genetic modification can increase the acetyl-CoA or malonyl-CoA levels. In some embodiments, the additional genetic modification comprises: 1) the elimination or the reduction of a *Yarrowia lipolytica* gene selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof; and/or 2) the overexpression of a *Yarrowia lipolytica* gene selected from the group consisting of Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0C03025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydro-lyase) (MFE1; YALI0E15378), primary oleate regulator (POR1; YALI0D12628), or a combination thereof.

In one embodiment, the additional genetic modification can increase the acetyl-CoA or malonyl-CoA levels. In some embodiments, the additional genetic modification comprises: 1) the elimination or the reduction of a *Yarrowia lipolytica* gene selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), or a combination thereof; and/or 2) the overexpression of a *Yarrowia lipolytica* gene selected from the group consisting of Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0C03025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), or a combination thereof.

In some embodiments, the additional genetic modification consists essentially of: 1) the elimination or the reduction of one or more *Yarrowia lipolytica* genes selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof; and/or 2) the overexpression of one or more *Yarrowia lipolytica* genes selected from the group consisting of Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0C03025), Acetaldehyde Dehydrogenase 3 (ALD3;

YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydrolyase) (MFE1; YALI0E15378), primary oleate regulator (POR1; YALI0D12628), or a combination thereof.

In some embodiments, the additional genetic modification consists of 1) the elimination or the reduction of a *Yarrowia lipolytica* gene selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof; and/or 2) the overexpression of a *Yarrowia lipolytica* gene selected from the group consisting of Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0003025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydro-lyase) (MFE1; YALI0E15378), primary oleate regulator (POR1; YALI0D12628), or a combination thereof.

In one embodiment, the additional genetic modification is overexpression of Pyruvate Decarboxylase (Pyrudecarb (PDC1); YALI0D10131p). In one embodiment, the additional genetic modification is overexpression of Malate Dehydrogenase (MAE1; YALI0E18634p). In one embodiment, the additional genetic modification is overexpression of ATP-Citrate Lyase Subunit 1 (ACL1; YALI0E34793p). In one embodiment, the additional genetic modification is overexpression of ATP-Citrate Lyase Subunit 2 (ACL2; YALI0D24431p). In one embodiment, the additional genetic modification is overexpression of Pyruvate Dehydrogenase E1 Component Subunit Alpha (PDC-E1; YALI0F20702p). In one embodiment, the additional genetic modification is overexpression of Acetyl-CoA Carboxylase (AceCarb (ACC1); YALI0C11407g). In one embodiment, the additional genetic modification is overexpression of Acetyl-CoA Synthetase (AceCoA; YALI0F05962g).

In some embodiments, the additional genetic modification comprises the elimination or the reduction of *Yarrowia lipolytica* gene phosphatidate phosphatase (PAH1; YALI0D27016); and/or the additional genetic modification comprises the overexpression of one or more *Yarrowia lipolytica* genes selected from the group consisting of peroxin 10 (PEX10; YALI0C01023), multifunctional β oxidation protein (oxidoreductase and hydro-lyase) (MFE1; YALI0E15378), primary oleate regulator (POR1; YALI0D12628), or a combination thereof.

In one embodiment, the *Yarrowia lipolytica* yeast cell is a wild-type strain. In a further embodiment, the wild-type strain is a PO1f strain. In an additional embodiment, the *Yarrowia lipolytica* yeast cell has been preoptimized for lipid overproduction. In one embodiment, the yeast cell is an L36 strain. A strain of *Y. lipolytica*, dubbed L36, was identified as displaying remarkable triacylglyceride accumulation ability. Whole-genome sequencing of this strain pinpointed a mutation in the MGA2 transcriptional regulator as the most likely genomic explanation. Complementation assays of an MGA2p truncation mutant into wildtype background reached 50% of L36 lipid levels.

By using each of the heterologous genes, the genetically modified yeast cell can be used to make a number of target Type III polyketide molecules. The Type III polyketide target molecules that can be synthesized from the genetically modified yeast cell (containing the heterologous genes listed above) include for example, triacetic acid lactone (TAL) (CAA86219.2 (*Gerbera hybrida*)), aloesone (AY517486 (*Rheum palmatum*)), phloroglucinol (JX840717-JX840724 (*Pseudomonas fluorescens*)), benzalacetone (B0LDU5 (*Rubus idaeus*)), 1,8-dihydroxynaphthalene and flaviolin (B1VLQ8 (*Streptomyces griseus*)), 1,8-dihydroxynaphthalene (SCO1206 (*Streptomyces coelicolor*)), and phloroisovalerophenone (BAB12102.2 (*Humulus lupulus*)).

Other genetic changes to the yeast strain can also help improve the production of the targeted Type III polyketide. In some embodiments, the yeast cell is genetically modified to either knockout (gene expression is eliminated) or knockdown (gene expression is reduced) a gene, wherein the genetically modified yeast strain has an enhanced availability of acetyl-CoA and/or malonyl-CoA. In some embodiments, the genes that may be the targets for knockout or knockdown include, for example: Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2

(ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof.

In some embodiments, the yeast cell is genetically modified to overexpress a gene, wherein the genetically modified yeast strain has an enhanced availability of acetyl-CoA and/or malonyl-CoA. In some embodiments, the genes that may be the targets for overexpression include, for example: Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0O03025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydro-lyase) (MFE1; YALI0E15378), primary oleate regulator (POR1; YALI0D12628), or a combination thereof.

In some embodiments, the yeast cell is genetically modified to either knockout (gene expression is eliminated) or knockdown (gene expression is reduced) a gene, wherein the genetically modified yeast strain has an enhanced availability of acetyl-CoA and/or malonyl-CoA. In some embodiments, the genes that may be the targets for knockout or knockdown include, for example: Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), or a combination thereof.

In some embodiments, the yeast cell is genetically modified to overexpress a gene, wherein the genetically modified yeast strain has an enhanced availability of acetyl-CoA and/or malonyl-CoA. In some embodiments, the genes that may be the targets for overexpression include, for example: Acetyl-CoA Carboxylase (AceCarb (ACC1); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0O03025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), or a combination thereof.

In some embodiments, the genes are overexpressed from a plasmid. In some embodiments, the genes are overexpressed from an integrated construct. In some embodiments, the promoter used to overexpress the gene is a constitutive promoter. In some embodiments, the promoter used to overexpress the gene is a conditional promoter (for example, a promoter that changes expression based on the culture conditions, such as different carbon sources).

In some embodiments, the recombinant nucleic acid encodes a protein comprising a mutation relative to the wildtype protein. In embodiments, the mutation is a point mutation. In embodiments, the mutation is a deletion. In embodiments, the mutation is an insertion. In embodiments, the mutation is a fusion with a second protein.

In some embodiments, the genetic modification increases the level of acetyl-CoA in the genetically modified oleaginous organism (e.g. yeast cell, oleaginous yeast cell, *Yarrowia lipolytica*) relative to a genetically unmodified oleaginous organism (e.g. yeast cell, oleaginous yeast cell, *Yarrowia lipolytica*) that is otherwise identical (e.g. genetically) to the genetically modified oleaginous organism (e.g. yeast cell, oleaginous yeast cell, *Yarrowia lipolytica*). In some embodiments, the genetic modification increases the level of malonyl-CoA in the genetically modified oleaginous organism (e.g. yeast cell, oleaginous yeast cell, *Yarrowia lipolytica*) relative to a genetically unmodified oleaginous organism (e.g. yeast cell, oleaginous yeast cell, *Yarrowia lipolytica*, algae) that is otherwise identical (e.g. genetically) to the genetically modified oleaginous organism (e.g. yeast cell, oleaginous yeast cell, *Yarrowia lipolytica*).

Carbon Sources

An array of Type III polyketides can be made from a variety of starting carbon sources. Examples of these carbon sources include, for example, glucose, glycerol, xylose, fructose, mannose, ribose, sucrose, and lignocellulosic biomass. In some embodiments, the carbon source can be ethanol or acetate. In one embodiment, the carbon source is glucose.

Alternative carbon sources can lead to a varied CoA precursor pool. With varied CoA precursors derived from sources like lignin, there is an entire suite of polyketide synthases that can be investigated for the production of various polyketide molecules. By feeding in these CoA precursors and using the host's own malonyl-CoA production, there is no need to engineer the yeasts to make their own novel CoAs. This allows metabolism to be more focused on the production of the final chemical target.

In some embodiments, an oleaginous yeast may be cultured using a medium comprising one or more carbon sources selected from the group consisting of glucose, fructose, sucrose, lactose, galactose, xylose, mannose, rhamnose, arabinose, glycerol, acetate, depolymerized sugar beet pulp, black liquor, corn starch, depolymerized cellulosic material, corn stover, sugar beet pulp, switchgrass, milk whey, molasses, potato, rice, sorghum, sugar cane, wheat, and mixtures thereof (e.g. mixtures of glycerol and glucose, mixtures of glucose and xylose, mixtures of fructose and glucose, mixtures of sucrose and depolymerized sugar beet pulp, black liquor, corn starch, depolymerized cellulosic material, corn stover, sugar beet pulp, switchgrass, milk whey, molasses, potato, rice, sorghum, sugar cane, and/or wheat). In embodiments, an oleaginous yeast is cultured using a medium comprising lignocellulosic biomass.

In some embodiments, carbon sources may be monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, or barley malt). Additionally, carbon sources may include alkanes, fatty acids, esters of fatty acids, monoglycerides, diglycerides, triglycerides, phospholipids, various commercial sources of fatty acids including vegetable oils (e.g., soybean oil) or animal fats.

In some embodiments, the growth medium comprises a majority carbon source selected from the group consisting of glucose, glycerol, xylose, fructose, mannose, ribose, sucrose, and lignocellulosic biomass. In one embodiment, the growth medium comprises glucose as the majority carbon source.

In some embodiments, the culture medium may contain, in addition to the primary, or majority carbon source, one or more secondary carbon sources. In some embodiments, the secondary carbon source comprises lignin or lignin derived aromatic compounds. In some embodiments, the secondary carbon source comprises lignin breakdown products. In some embodiments, the lignin breakdown products include, for example, paracoumaryl, coniferyl and sinapyl acids. In some embodiments, the secondary carbon source can include lignan derived compounds including secoisolariciresinol, matairesinol, lariciresinol, and pinoresinol. In some embodiments, the co-A molecule is derived from acids, including, for example, p-coumaric acid, trans-ferulic acid, 3-phenylpropanoic acid, octanoic acid, trans-cinnamic acid, 3-fluorocinnamic acid, benzoic acid, 3-aminobenzoic acid, propanoic acid, 2-bromobenzoic acid, phenylacetic acid, phenylpyruvic acid, pentanoic acid, methylmalonic acid, ethylmalonic acid, chloromalonic acid, cinamic acid, and other aliphatic acids.

Culture conditions and growth medium for oleaginous yeast cells are known in the art. See for example, WO2014179748; Blazeck, J. et al. Metab Eng. 2015 Nov. 32:66-73; Liu, L. et al. Metab Eng. 2015 Sep. 31:102-11; Blazeck, J. et al. Nat Commun. 2014 5:3131; Blazeck, J. et al. J Biotechnol. 2013 Jun. 165(3-4):184-94; which are hereby incorporated by reference.

Methods of Polyketide Production

The genetically modified yeast strains disclosed herein can be used for the increased production of Type III polyketides.

Disclosed herein is a method for the production of a Type III polyketide comprising: 1) culturing an oleaginous yeast cell in a growth medium, wherein the yeast cell comprises a heterologous gene, wherein the heterologous gene encodes a Type III polyketide synthase; and 2) isolating said Type III polyketide.

Disclosed herein is a method for the production of a Type III polyketide comprising: 1) culturing an oleaginous yeast cell in a growth medium, wherein the yeast cell comprises a heterologous gene, wherein the heterologous gene encodes a Type III polyketide synthase selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, and BAB12102.2 gene from *Humulus lupulus*; and 2) isolating said Type III polyketide.

In another embodiment, disclosed herein is a method for the production of a Type III polyketide comprising: 1) culturing a *Yarrowia lipolytica* yeast cell in a growth medium, wherein the yeast cell comprises one or more heterologous genes selected from the group consisting of the CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, and BAB12102.2 gene from *Humulus lupulus*; and 2) isolating said Type III polyketide.

In one embodiment, the heterologous gene is the CAA86219.2 gene from *Gerbera hybrida*. In one embodiment, the heterologous gene is the AY517486 gene from *Rheum palmatum*. In one embodiment, wherein the heterologous gene is the JX840717-JX840724 gene from *Pseudomonas fluorescens*. In one embodiment, the heterologous gene is the B0LDU5 gene from *Rubus idaeus*. In one embodiment, the heterologous gene is the B1VLQ8 gene from *Streptomyces griseus*. In one embodiment, the heterologous gene is the SCO1206 gene from *Streptomyces coelicolor*, In one embodiment, the heterologous gene is the BAB12102.2 gene from *Humulus lupulus*.

In some embodiments, the Type III polyketide is selected from the group consisting of Triacetic Acid Lactone, Aloesone, Phloroglucinol, Benzalacetone, 1,8-Dihydroxynaphthalene, flaviolin, and phloroisovalerophenone. In one embodiment, the Type III polyketide is Triacetic Acid Lactone. In one embodiment, the Type III polyketide is Aloesone. In one embodiment, the Type III polyketide is Phloroglucinol. In one embodiment, the Type III polyketide is Benzalacetone. In one embodiment, the Type III polyketide is 1,8-Dihydroxynaphthalene. In one embodiment, the Type III polyketide is flaviolin. In one embodiment, the Type III polyketide is phloroisovalerophenone.

In one embodiment, the heterologous gene is integrated into the genome of the yeast cell. In another embodiment, at least two copies of the heterologous gene are present in the genome of the yeast cell. In one embodiment, the heterologous gene is incorporated into a gene expression cassette comprising a promoter and the heterologous gene, wherein the gene expression cassette is integrated into the genome of the yeast cell. In an alternative embodiment, the heterologous gene is episomally expressed from a plasmid.

Other genetic changes to the yeast strain can also help improve the production of the targeted Type III polyketide. In another aspect, the genetically modified *Yarrowia lipolytica* yeast cell comprises an additional genetic modification. For example, the additional genetic modification can increase the acetyl-CoA or malonyl-CoA levels. In some embodiments, the additional genetic modification comprises 1) the elimination or the reduction of one or more *Yarrowia lipolytica* genes selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof; and/or 2) the overexpression of one or more *Yarrowia lipolytica* genes selected from the group consisting of Acetyl-CoA Carboxylase (AceCarb (ACC1); YALI0C11407g, Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0003025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydrolyase) (MFE1; YALI0E15378), primary oleate regulator (POR1; YALI0D12628), or a combination thereof.

In one embodiment, the additional genetic modification is overexpression of Pyruvate Decarboxylase (Pyrudecarb (PDC1); YALI0D10131p). In one embodiment, the additional genetic modification is overexpression of Malate Dehydrogenase (MAE1; YALI0E18634p). In one embodiment, the additional genetic modification is overexpression of ATP-Citrate Lyase Subunit 1 (ACL1; YALI0E34793p). In one embodiment, the additional genetic modification is overexpression of ATP-Citrate Lyase Subunit 2 (ACL2; YALI0D24431p). In one embodiment, the additional genetic modification is overexpression of Pyruvate Dehydrogenase E1 Component Subunit Alpha (PDC-E1; YALI0F20702p). In one embodiment, the additional genetic modification is overexpression of Acetyl-CoA Carboxylase (AceCarb (ACC1); YALI0C11407g). In one embodiment, the additional genetic modification is overexpression of Acetyl-CoA Synthetase (AceCoA; YALI0F05962g). In one embodiment, the additional genetic modification is overexpression of peroxin 10 (PEX10; YALI0C01023). In one embodiment, the additional genetic modification is overexpression of multifunctional β oxidation protein (oxidoreductase and hydro-lyase) (MFE1; YALI0E15378). In one embodiment, the additional genetic modification is overexpression of primary oleate regulator (POR1; YALI0D12628).

In a further embodiment, the *Yarrowia lipolytica* yeast cell is a PO1f strain. In an additional embodiment, the *Yarrowia lipolytica* yeast cell is an L36 strain. A strain of *Y. lipolytica*, dubbed L36, was identified as displaying remarkable triacylglyceride accumulation ability. Whole-genome sequencing of this strain pinpointed a mutation in the MGA2 transcriptional regulator as the most likely genomic explanation. Complementation assays of an MGA2p truncation mutant into wildtype background reached 50% of L36 lipid levels.

By using each of the heterologous genes, the genetically modified yeast cell can be used to make a number of target Type III polyketide molecules. The Type III polyketide target molecules that can be synthesized from the genetically modified yeast cell containing the heterologous genes above include for example, triacetic acid lactone (TAL) (CAA86219.2 (*Gerbera hybrida*)), aloesone (AY517486 (*Rheum palmatum*)), phloroglucinol (JX840717-JX840724 (*Pseudomonas fluorescens*)), benzalacetone (B0LDU5 (*Rubus idaeus*)), 1,8-dihydroxynaphthalene and flaviolin (B1VLQ8 (*Streptomyces griseus*)), 1,8-dihydroxynaphthalene (SCO1206 (*Streptomyces coelicolor*)), and phloroisovalerophenone (BAB12102.2 (*Humulus lupulus*)).

Other genetic changes to the yeast strain can also help improve the production of the targeted Type III polyketide. In some embodiments, the yeast cell is genetically modified to either knockout (gene expression is eliminated) or knockdown (gene expression I s reduced) a gene, wherein the genetically modified yeast strain has an enhanced availability of acetyl-CoA and/or malonyl-CoA. In some embodiments, the genes that may be the targets for knockout or knockdown include, for example: Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof In some embodiments, the yeast cell is genetically modified to overexpress a gene, wherein the genetically modified yeast strain has an enhanced availability of acetyl-CoA and/or malonyl-CoA. In some embodiments, the genes that may be the targets for overexpression include, for example: Acetyl-CoA Carboxylase (AceCarb (ACC); YALI0C11407g), Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Putative Pyruvate Decarboxylase 2 (PDC2; YALI0D06930), Acetyl-CoA Synthetase 1 (ACS1; YALI0F05962), Acetaldehyde Dehydrogenase 1 (ALD1; YALI0B01298), Acetaldehyde Dehydrogenase 2 (ALD2; YALI0O03025), Acetaldehyde Dehydrogenase 3 (ALD3; YALI0E00264), Acetaldehyde Dehydrogenase 4 (ALD4; YALI0F23793), Acetaldehyde Dehydrogenase 5 (ALD5; YALI0D07942), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), peroxin 10 (PEX10; YALI0C01023), multifunctional β oxidation protein (oxidoreductase and hydro-lyase) (MFE1; YALI0E15378), primary oleate regulator (POR1; YALI0D12628), or a combination thereof.

In some embodiments, the genes are overexpressed from a plasmid. In some embodiments, the genes are overexpressed from an integrated construct. In some embodiments, the promoter used to overexpress the gene is a constitutive promoter. In some embodiments, the promoter used to overexpress the gene is a conditional promoter (for example, a promoter that increases expression in different carbon sources, for example, galactose).

In embodiments, the recombinant nucleic acid encodes a protein comprising a mutation relative to the wild-type protein. In embodiments, the mutation is a point mutation. In embodiments, the mutation is a deletion. In embodiments, the mutation is an insertion. In embodiments, the mutation is a fusion with a second protein.

In some embodiments of the method, the growth medium comprises a majority carbon source selected from the group consisting of glucose, glycerol, xylose, fructose, mannose, ribose, sucrose, and lignocellulosic biomass. In one embodiment, the growth medium comprises glucose as the majority carbon source.

Optional CoA ligases can also be included to provide the initial starting materials for the disclosed methods. In some cases, the methods disclosed herein further comprise the addition of molecules such as catechols, p-coumaroyl-CoA, feruloyl-coA, hydroxybenzoyl-CoA, and/or isovaleroyl-CoA. In some cases, the methods disclosed herein further comprise the addition of molecules such as paracoumaryl, coniferyl and sinapyl acids. In some embodiments, the methods disclosed herein further comprise the addition of molecules such as lignan derived compounds, including, for example, secoisolariciresinol, matairesinol, lariciresinol, and pinoresinol. In some embodiments, the derived CoA molecules originate from acids including, for example, p-coumaric acid, trans-ferulic acid, 3-phenylpropanoic acid, octanoic acid, trans-cinnamic acid, 3-fluorocinnamic acid, benzoic acid, 3-aminobenzoic acid, propanoic acid, 2-bromobenzoic acid, phenylacetic acid, phenylpyruvic acid, pentanoic acid, methylmalonic acid, ethylmalonic acid, chloromalonic acid, cinamic acid, and other aliphatic acids.

In addition to the key genetic alterations that have been disclosed herein, additional improvements in yield of Type III polyketides can occur due to culturing conditions that can solubilize the product and encourage product formulation. In one embodiment, a solubility agent may be added to increase the solubility of the Type III polyketide. In one embodiment, the solubility agent is gamma valerolactone. In one embodiment, the solubility agent is triethylene glycol.

In some embodiments, the yeast strains and methods disclosed herein are used to produce high levels of polyketides, for example, greater than 5 g/L. In some embodiments, the polyketide amounts produced are greater than 5 g/L, greater than 10 g/L, greater than 15 g/L, greater than 20 g/L, greater than 25 g/L, greater than 50 g/L, or greater than 100 g/L.

In some embodiments, the yeast strains are cultured between 20° C. and 40° C. In some embodiments, the yeast strains are cultured between 25° C. and 35° C.

In some embodiments, the yeast strains are cultured using a sugar feed amount between 0 and 250 g/L sugars. In some embodiments, the initial sugar feed is 20 g/L sugar (for example, glucose).

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Production of the Type III polyketide triacetic acid lactone (TAL) in *Yarrowia lipolytica*

Oleaginous yeast species were investigated as hosts for the production of Type III polyketides due to their already abundant precursor pools of CoA molecules. In some embodiments, the flux of these organisms can be shifted from the production of fatty acids to the production of polyketides. *Yarrowia lipolytica* is being used in this example to demonstrate the capacity of oleaginous yeast to produce Type III polyketides through the production of the Type III polyketide triacetic acid lactone (TAL).

Strain and Pathway Engineering

In order to improve the production of Type III polyketide production, a variety of gene targets have been identified for both knockdown and overexpression. By balancing metabolism and cofactors, a larger available pool of precursors can be fed into the production of polyketides. These targets relate to pathways for enhancing available acetyl-CoA and malonyl-CoA. All gene and protein sequences are available from the National Center for Biotechnology Information (www.ncbi.nlm.nih.gov) or the Genolevures: Genomic Exploration of the Hemiascomycete Yeasts website (www.genolevures.org).

TABLE 1

Knockout or Knockdown Targets

| Gene Identifier | Name | Abbreviation |
|---|---|---|
| YALI0F27071p | Aspartyl Protease | PEP4 |
| YALI0B16500p | Protease B Vacuolar | PRB1 |
| YALI0A06435g | Protease B Vacuolar | PRB1H |
| YALI0F18502p | Glucose-starch Glucosyltransferase Isoform 1 | GSY1 |
| YALI0E22649p | Glucose-6-phosphate Dehydrogenase | ZWF1 |
| YALI0C24101p | Pyruvate Carboxylase 1 | PYC1 |
| YALI0C16995p | Phosphoenolpyruvate Carboxykinase | PCK1 |
| YALI0A15972p | Fructose-1,6-bisphosphatase | FBP1 |
| YALI0E16478g | Mitochondrial Carrier | YIA6 |
| YALI0F05500g | Mitochondrial Carrier Protein | RIM2 |
| YALI0D25630p | Alcohol Dehydrogenase 1 | ADH1 |
| YALI0E17787p | Alcohol Dehydrogenase 2 | ADH2 |
| YALI0A16379p | Alcohol Dehydrogenase 3 | ADH3 |
| YALI0F30745p | C1-tetrahydrofolate Synthase | MIS1 |
| YALI0E01056g | C1-THFS Protein C1-Tetrahydrofolate Synthase Precursor Mitochondrial | MTHFD1L |
| YALI0E02090p | Phosphoglucomutase | PGM2 |
| YALI0B02948p | Glycerol-3-phosphate Dehydrogenase | GPD1 |
| YALI0B19382p | Fatty Acid Synthase Subunit Alpha | FAS2 |
| YALI0B15059p | Fatty Acid Synthase Subunit Beta | FAS1 |

TABLE 2

Overexpression Targets

| Gene Identifier | Name | Abbreviation |
|---|---|---|
| YALI0C11407g | Acetyl-CoA Carboxylase | AceCarb (ACC1) |
| YALI0D10131p | Pyruvate Decarboxylase | Pyrudecarb (PDC1) |
| YALI0D20768g | Dihydrolipoamide Dehydrogenase | PDE3 |
| YALI0D23683g | Dihydrolipoamide Acetyltransferase | PDE2 |
| YALI0E18634p | Malate Dehydrogenase | MAE1 |
| YALI0F05962g | Acetyl-CoA Synthetase | AceCoA |
| YALI0F20702p | Pyruvate Dehydrogenase E1 Component Subunit Alpha | PDC-E1 |
| YALI0E34793p | ATP-Citrate Lyase Subunit 1 | ACL1 |
| YALI0D24431p | ATP-Citrate Lyase Subunit 2 | ACL2 |
| YALI0E11495p | AMP Deaminase | AMPD |
| YALI0E30965g | Acetyl-CoA hydrolase | ACH1 |

Type III Polyketide Synthases

Sources of pathway enzyme for Type III polyketides have been explored. These pathways for polyketide production can be explored while at the same time taking advantage of the general promiscuity of these enzymes to produce derivative molecules. Non-limiting examples of initial Type III polyketide synthases identified for polyketide production in *Yarrowia lipolytica* are listed in Table 3 below.

TABLE 3

Examples of Type III polyketide Synthases

| Gene Identifier | Native Host Organism | Target Molecule |
|---|---|---|
| CAA86219.2 | *Gerbera hybrida* | Triacetic Acid Lactone |
| AY517486 | *Rheum palmatum* | Aloesone |
| JX840717-JX840724 | *Pseudomonas fluorescens* | Phloroglucinol |
| B0LDU5 | *Rubus idaeus* | Benzalacetone |
| B1VLQ8 | *Streptomyces griseus* | 1,8-Dihydroxynaphthalene and flaviolin |
| BAB12102.2 | *Humulus lupulus* | phloroisovalerophenone |

Optional CoA ligases can also be used to provide the initial starting materials. In some cases, molecules such as catechols, p-coumaroyl-CoA, feruloyl-coA, hydroxybenzoyl-CoA, and/or isovaleroyl-CoA may be used.

Carbon Sources

Alternative carbon sources can lead to a varied CoA precursor pool. With varied CoA precursors derived from sources like lignin, there is an entire suite of type III polyketide synthases that can be investigated for the production of various polyketide molecules. By feeding in these CoA precursors and using the host's own malonyl-CoA production, there is no need to engineer the yeasts to make their own novel CoAs. This allows metabolism to be more focused on the production of the final chemical target.

TAL Production Using the Type III Polyketide Synthase g2ps1 from *G. hybrida*

The type III polyketide synthase g2ps1 from the plant *Gerbera hybrida* was codon optimized through Blue Heron and integrated into the genome of *Y. lipolytica*. The activity of the codon optimized version of g2ps1 was assayed via reverse-phase HLPC. Two mutant variants of g2ps1 with increased activity have been created and characterized in *E. coli*. These mutations were replicated, taking into account codon bias in *Y. lipolytica*, by using site-directed mutagenesis. Expression was enabled by a synthetic, hybrid promoter designed for this host.

Strain Development

A variety of starting strains of *Y. lipolytica* were investigated for the production of TAL.

The production of TAL was seen in both the wild-type strain (PO1f) and a previously engineered strain for high lipid production (L36) (FIG. 1). In some examples, production of TAL was seen to be dependent on the leucine and uracil gene expressions as this seemed to vary across different strains.

Figure 2:
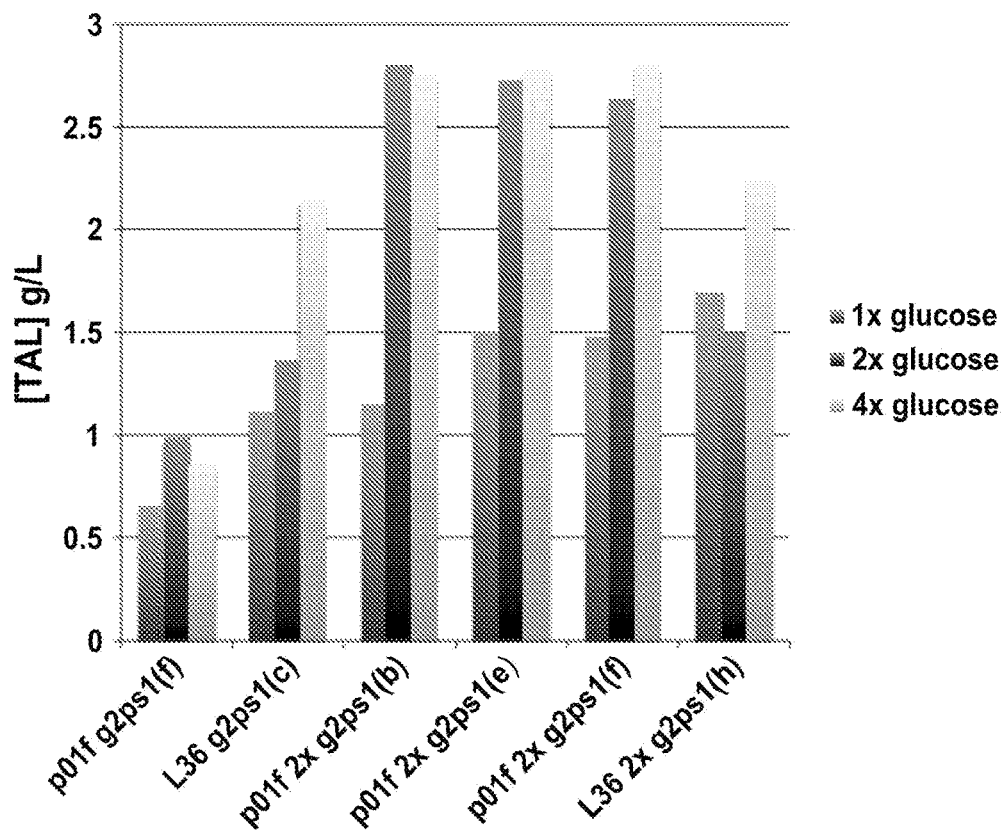
FIG. 2. Triacetic acid lactone (TAL) production increases with increased g2ps1 gene copies and increased amounts of glucose in wild type (PO1f) *Y. lipolytica* and a previously engineered *Y. lipolytica* strain for high lipid production (L36).

Next, the effect of multiple copies of g2ps1 was examined. It was observed that multiple copy expressions led to higher production titers (FIG. 2). In addition, higher levels of glucose led to increased amounts of TAL production.

The ability to scale up the reaction was examined using bioreactors. Two bioreactor runs were done according to the conditions in Table 4.

TABLE 4

Bioreactor Conditions

| | Run #1 | Run #2 |
|---|---|---|
| Strain | po1f S1 YCO g2ps1 | po1f S1 YCO g2ps1 |
| Temp (C.) | 28 | 28 |
| DO (%) | 50 | 50 |
| pH | 3.5 | 3.5 |
| Media | C80N10, Leu supplement | C80N10, Leu supplement |
| Starter OD | 0.1 | 0.1 |

Figure 3:
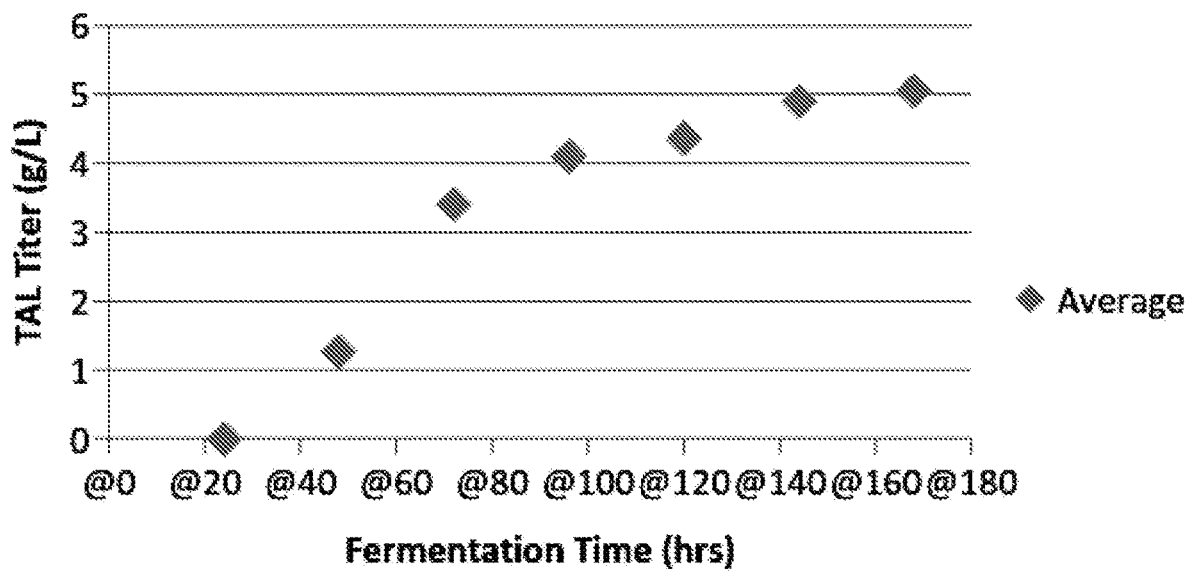
FIG. 3. Triacetic acid lactone (TAL) production (g/L) over time in Bioreactor Run #1.
Figure 4:
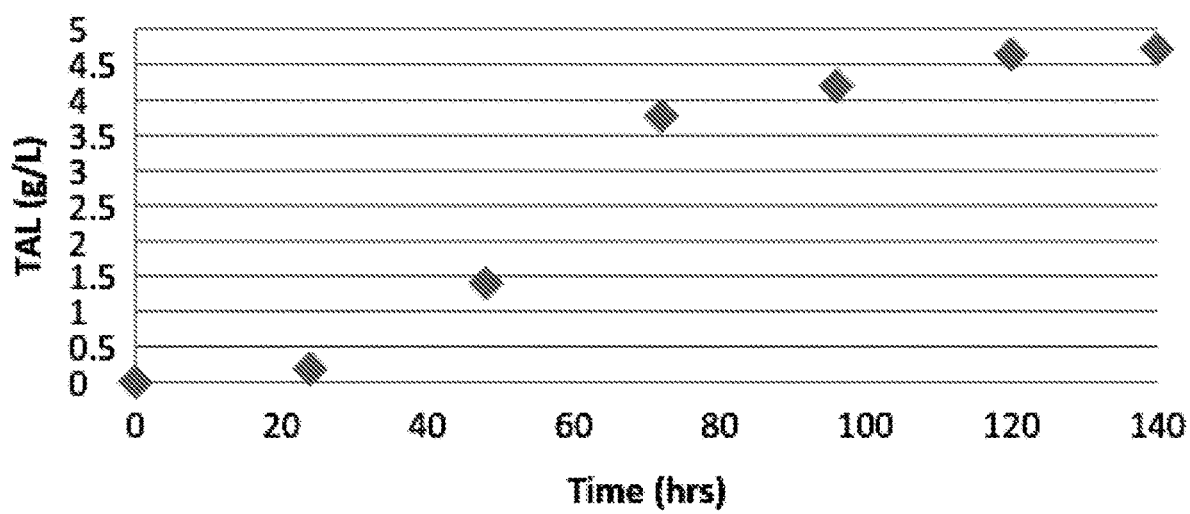
FIG. 4. Triacetic acid lactone (TAL) production (g/L) over time in Bioreactor Run #2.
Figure 5:
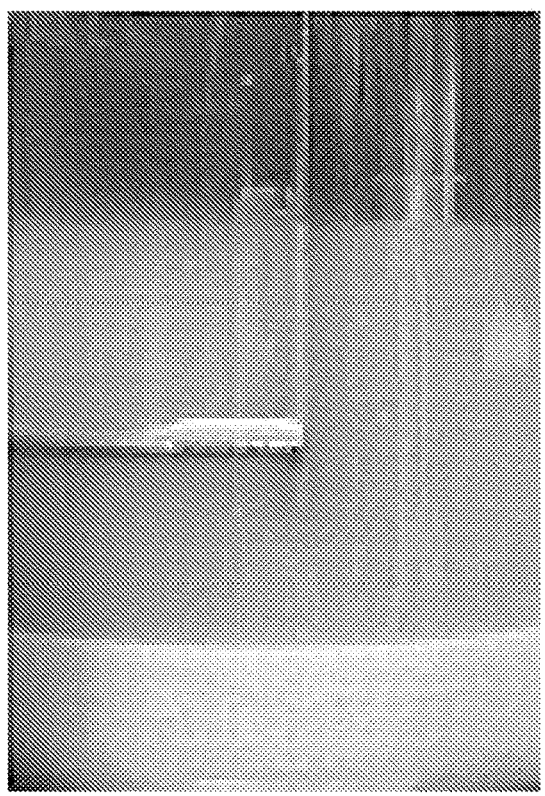
FIG. 5. Triacetic acid lactone (TAL) production can result in solubility issues, which are visualized easily when agitation is stopped and the reactor settles into distinct phases with crystalline TAL in the middle phase.

Due to solubility issues, these reported numbers (See FIGS. 3 and 4) are less than the actual titers. In additional HPLC runs using triethylene glycol as an additive to increase solubility, the final titer of reactor run #2 averages 5.6 g/L of TAL. These solubility issues are visualized easily when agitation is stopped and the reactor settles into distinct phases with crystalline TAL in the middle phase (FIG. 5).

Pathway Engineering

A number of genes from the over-expression targets listed in the table above (Table 2) were chosen for further analysis.

Figure 6:
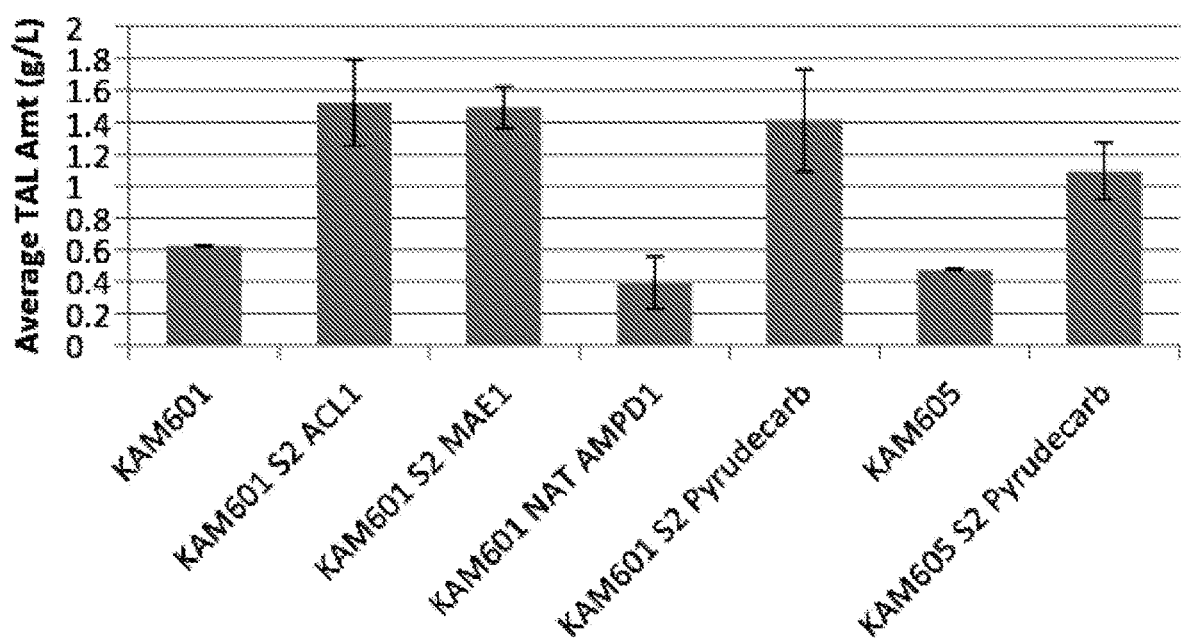
FIG. 6. Triacetic acid lactone (TAL) production is increased in yeast strains overexpressing ACL1, MAE1, or PDC1.
Figure 7:
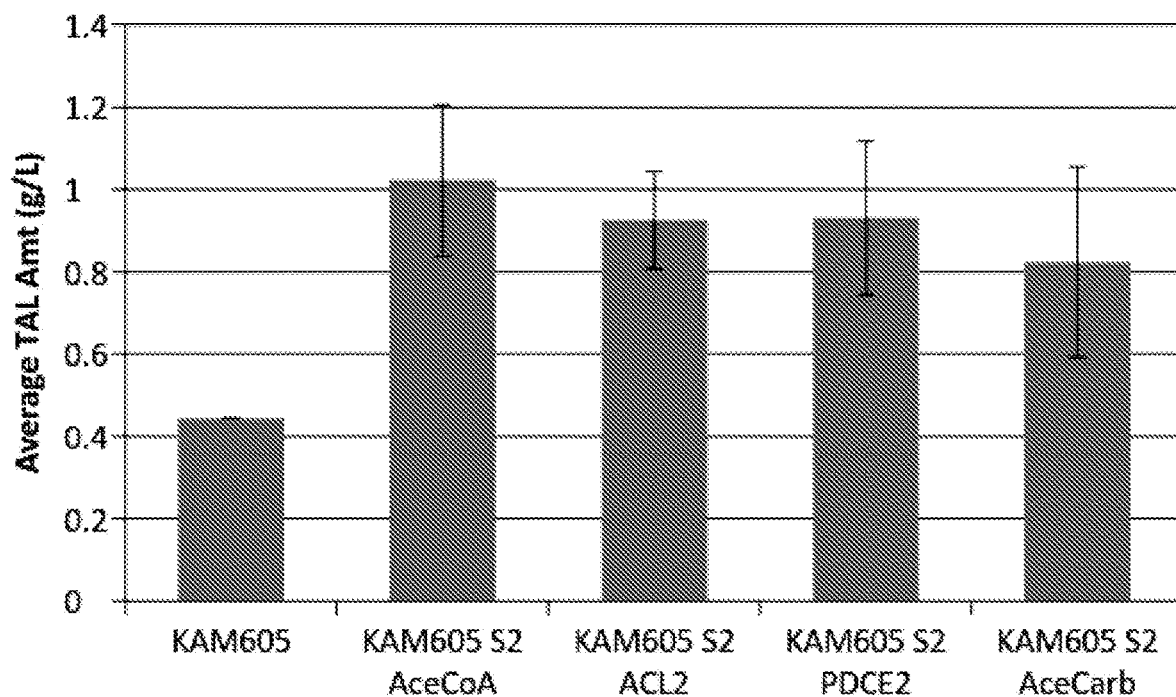
FIG. 7. Triacetic acid lactone (TAL) production is increased in yeast strains overexpressing AceCoA, ACL2, PDCE2, or AceCarb.
Figure 8:
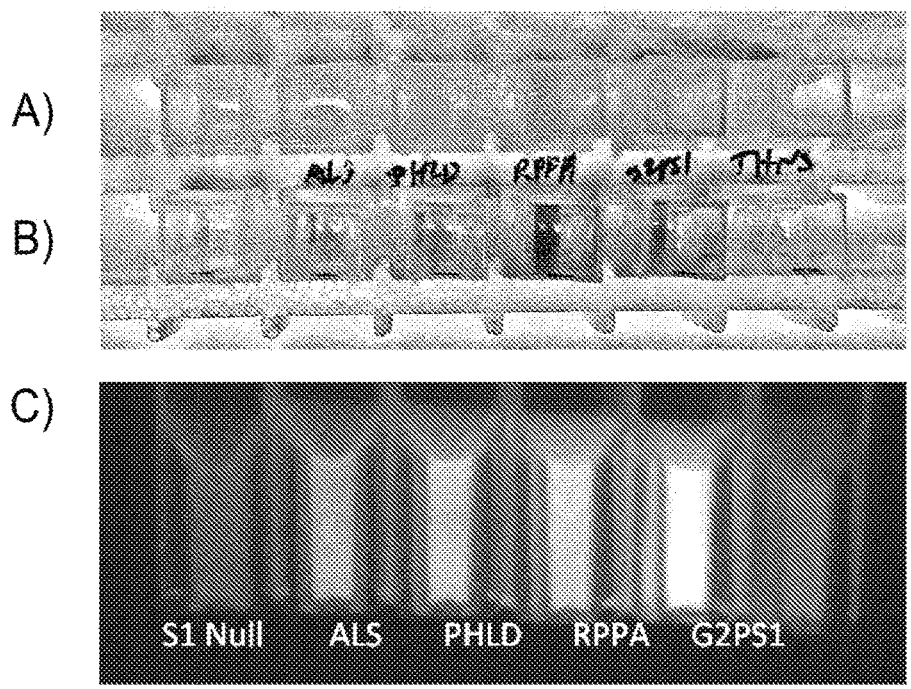
FIG. 8. The expression of five different PKS genes in wildtype *Yarrowia lipolytica* resulted in a qualitative change of pigments in: A) cells suspended in deionized water, B) cell culture supernatant, and C) suspended pellet under blue light.
Figure 9:
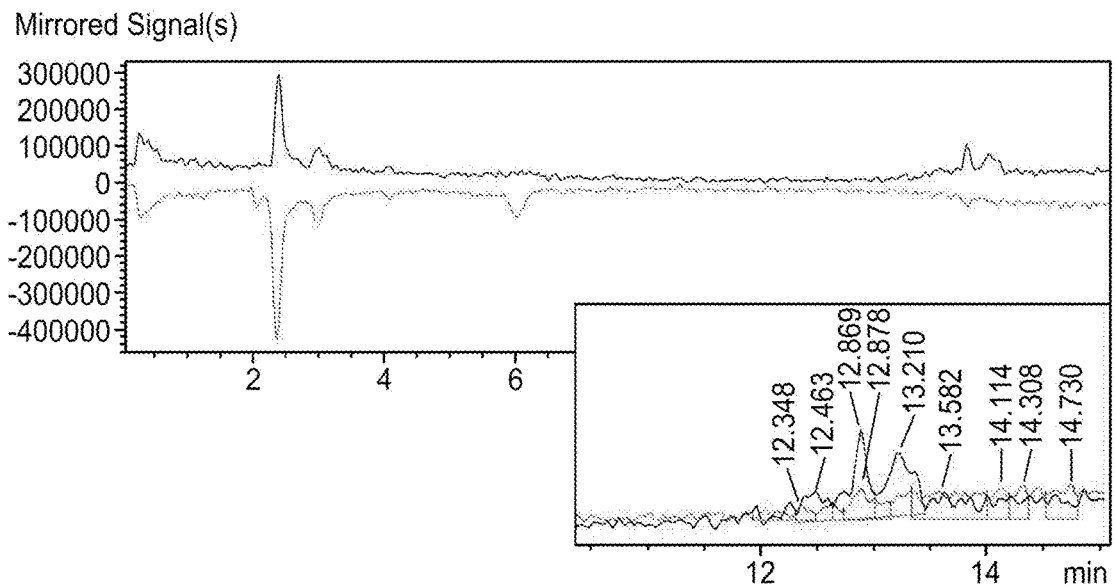
FIG. 9. Strain metabolite perturbations of PKS strains were measured using LC-MS. Novel peaks in pO1j ALS (blue) were identified at 12.869 and 13.210 minutes via LC-MS when compared to the wildtype chromatogram.
Figure 10:
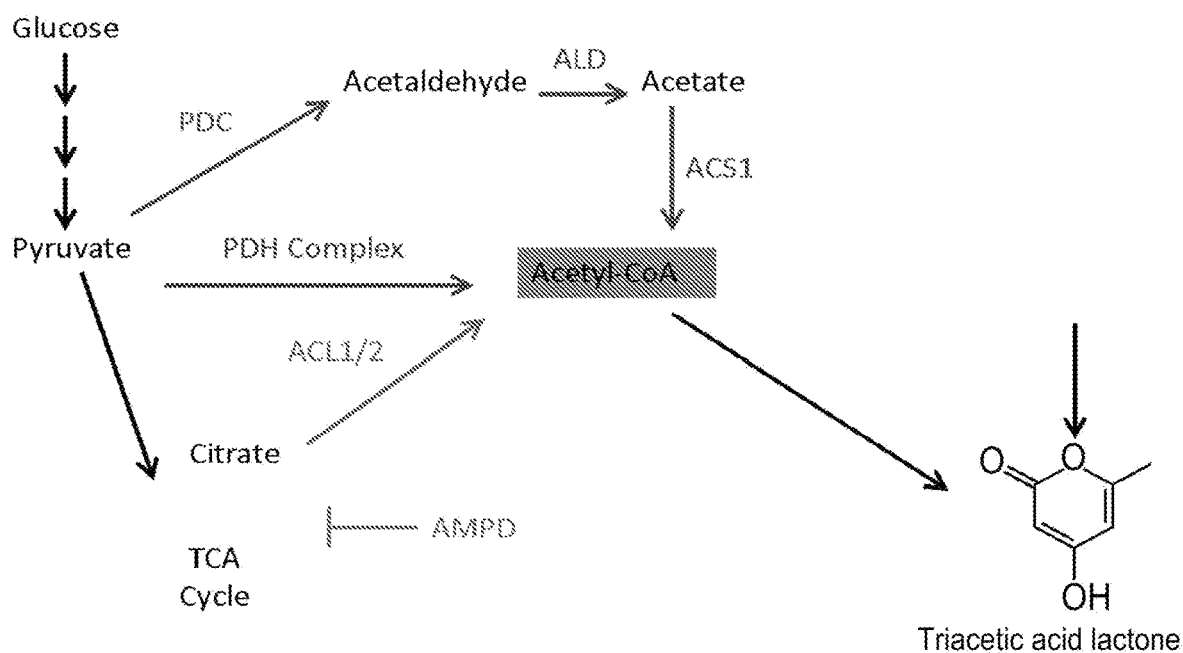
FIG. 10. Graphical depiction of overexpression targets related to the increased production of acetyl-CoA and malonyl-CoA to improve the titer of triacetic acid lactone (TAL).
Figure 11:
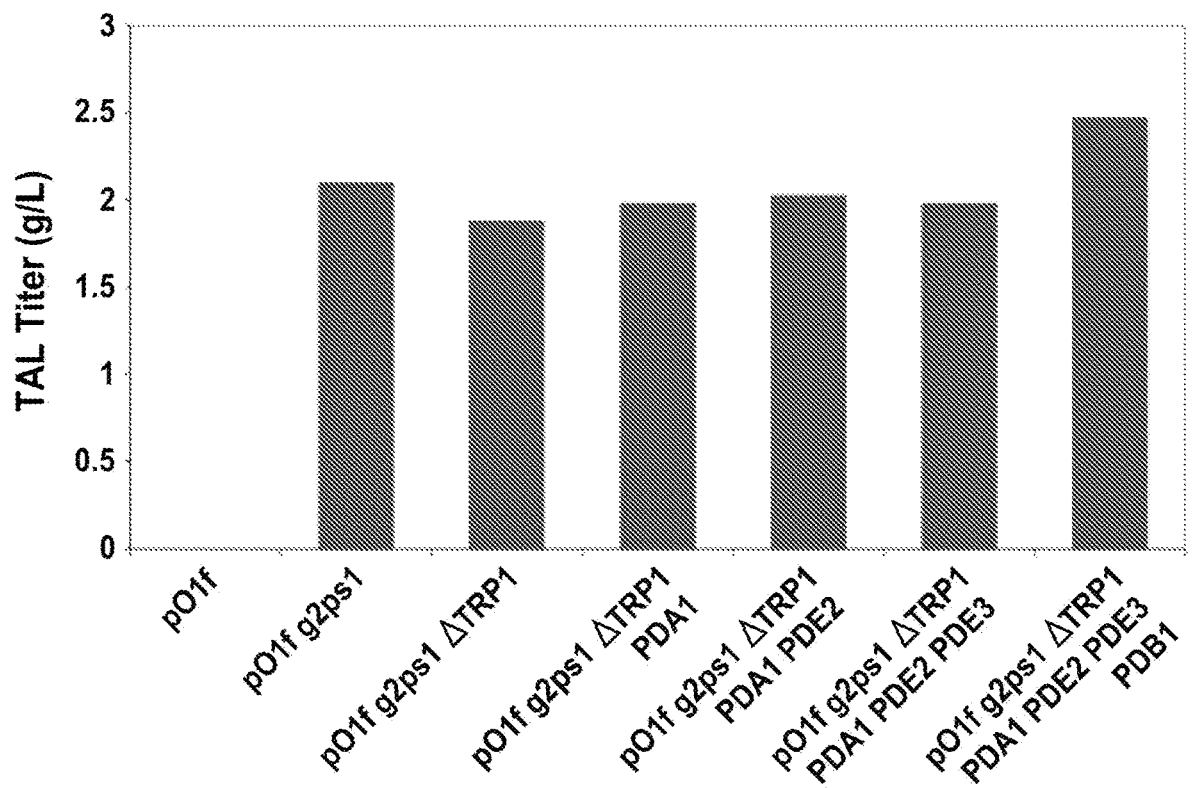
FIG. 11. The overexpression of the full pyruvate pathway PDH complex led to an increased production of TAL in a strain background containing four copies of g2ps 1, as measured by qPCR.
Figure 12:
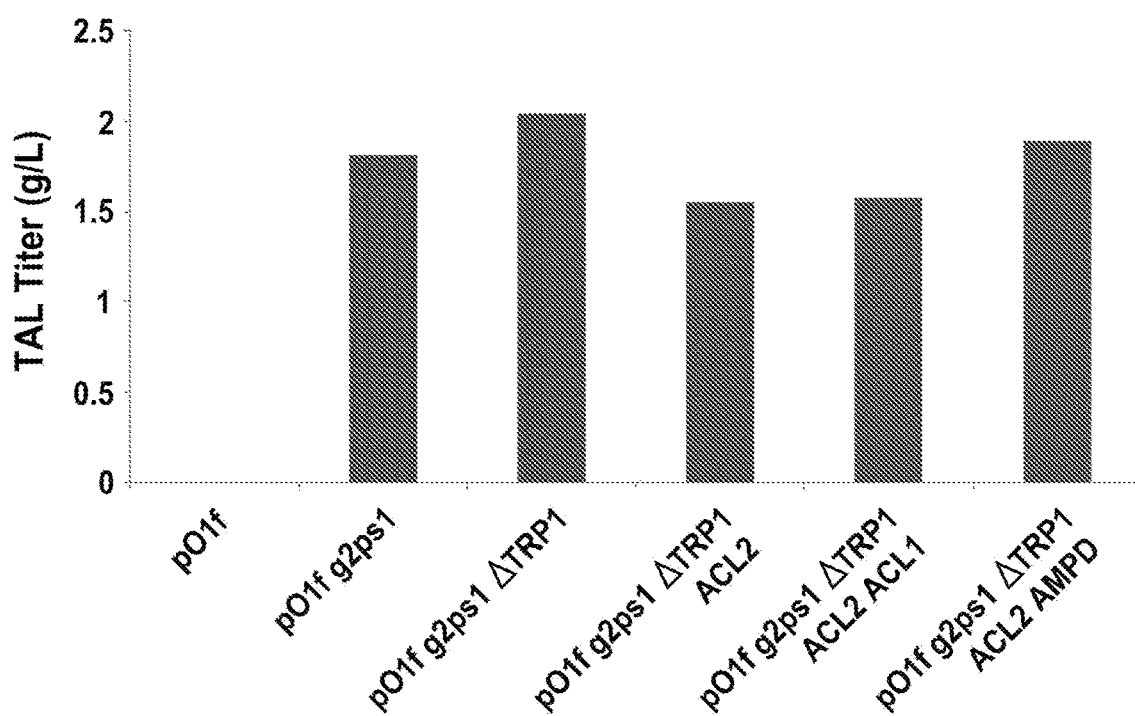
FIG. 12. The overexpression of ACL1 and ACL2 alone does not have a positive effect on TAL titers. Overexpression of AMPD with ACL1 and ACL2 improved titer, but still did not return production to levels prior to this additional engineering. AMPD alone will be overexpressed with and without ACC1 overexpression. As evidenced by increase in fatty acid titers, an increase in TAL titers is expected when AMPD is overexpressed.
Figure 13:
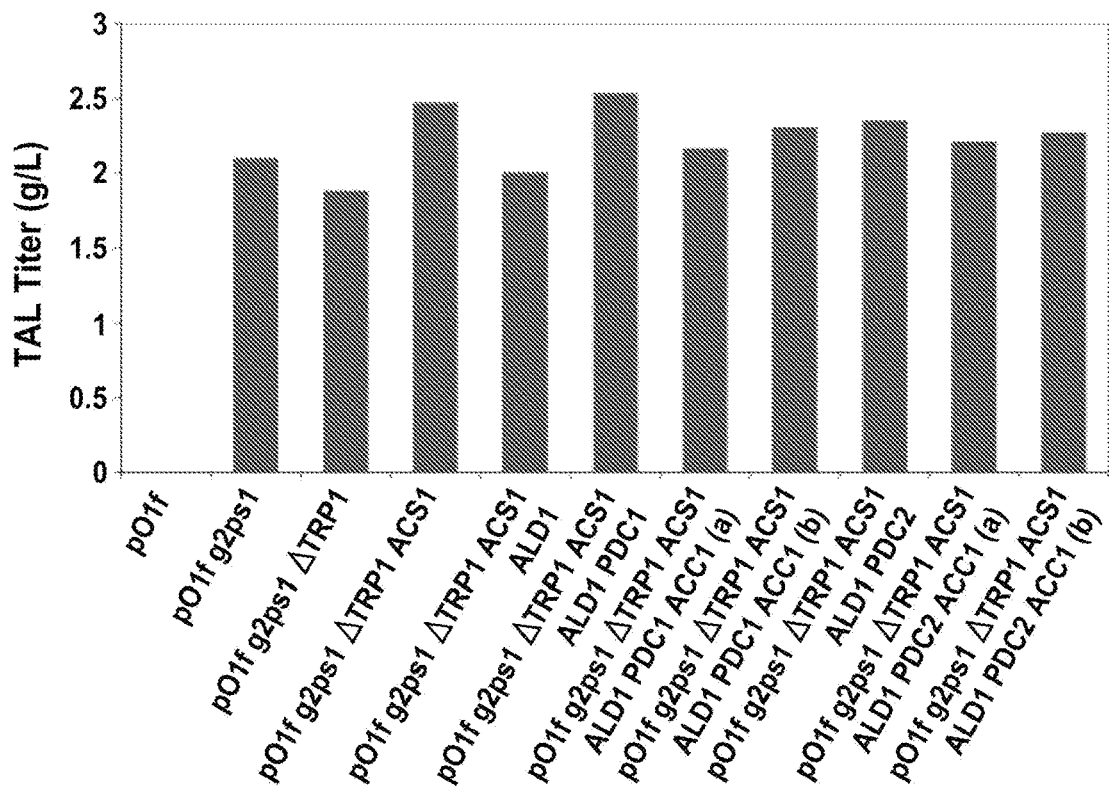
FIG. 13. Overexpression of genes through the acetate pathway (via ALD1) increased the titer of TAL produced in a strain background containing four copies of g2ps 1.
Figure 14:
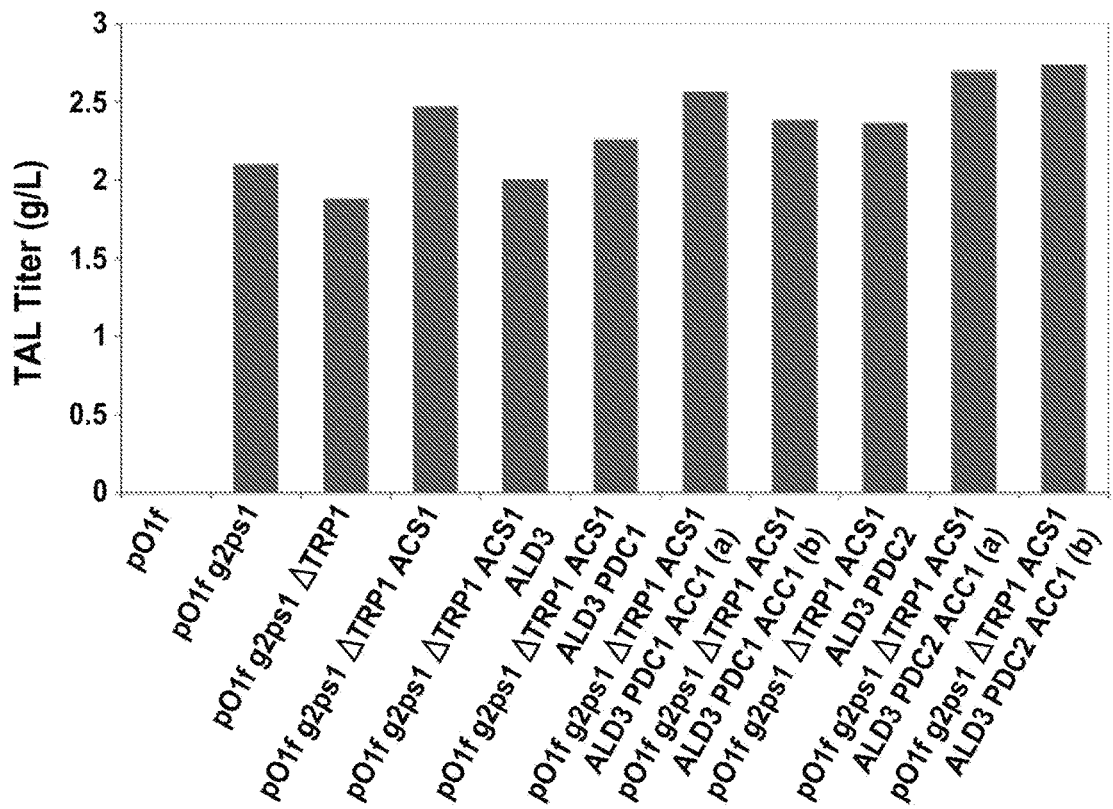
FIG. 14. Overexpression of genes through the acetate pathway (via ALD3) increased the titer of TAL produced in a strain background containing four copies of g2ps 1.
Figure 15:
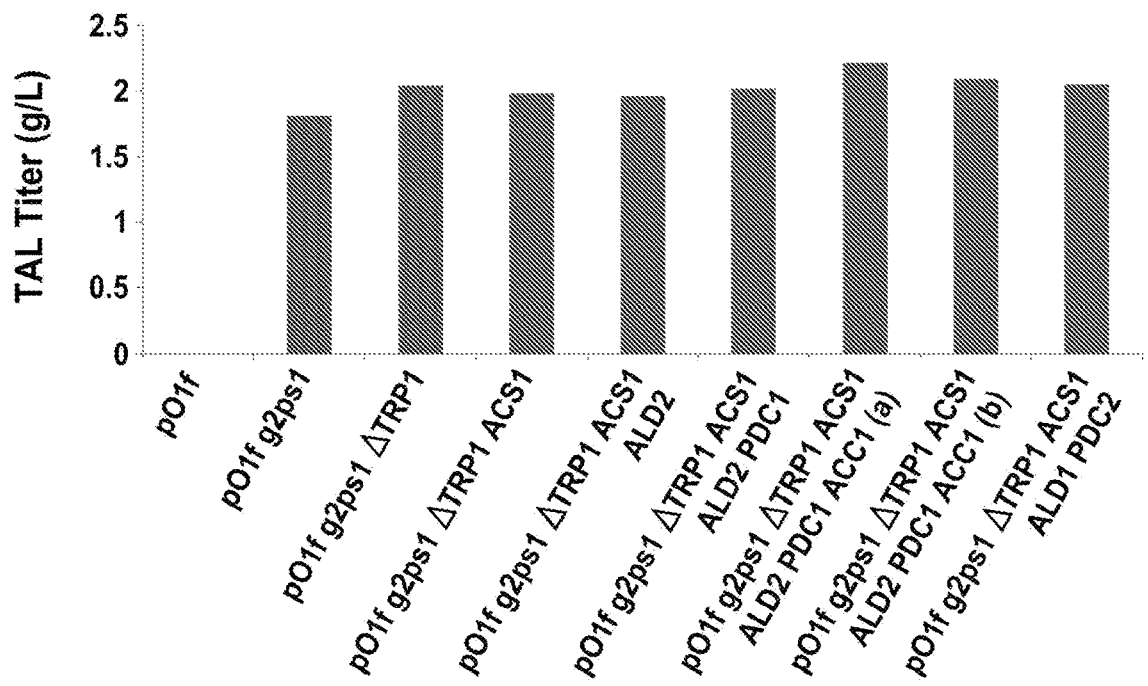
FIG. 15. Overexpression of genes through the acetate pathway (via ALD2) increased the titer of TAL produced in a strain background containing four copies of g2ps 1. ACC1 will be overexpressed in the strains containing PDC2.
Figure 16:
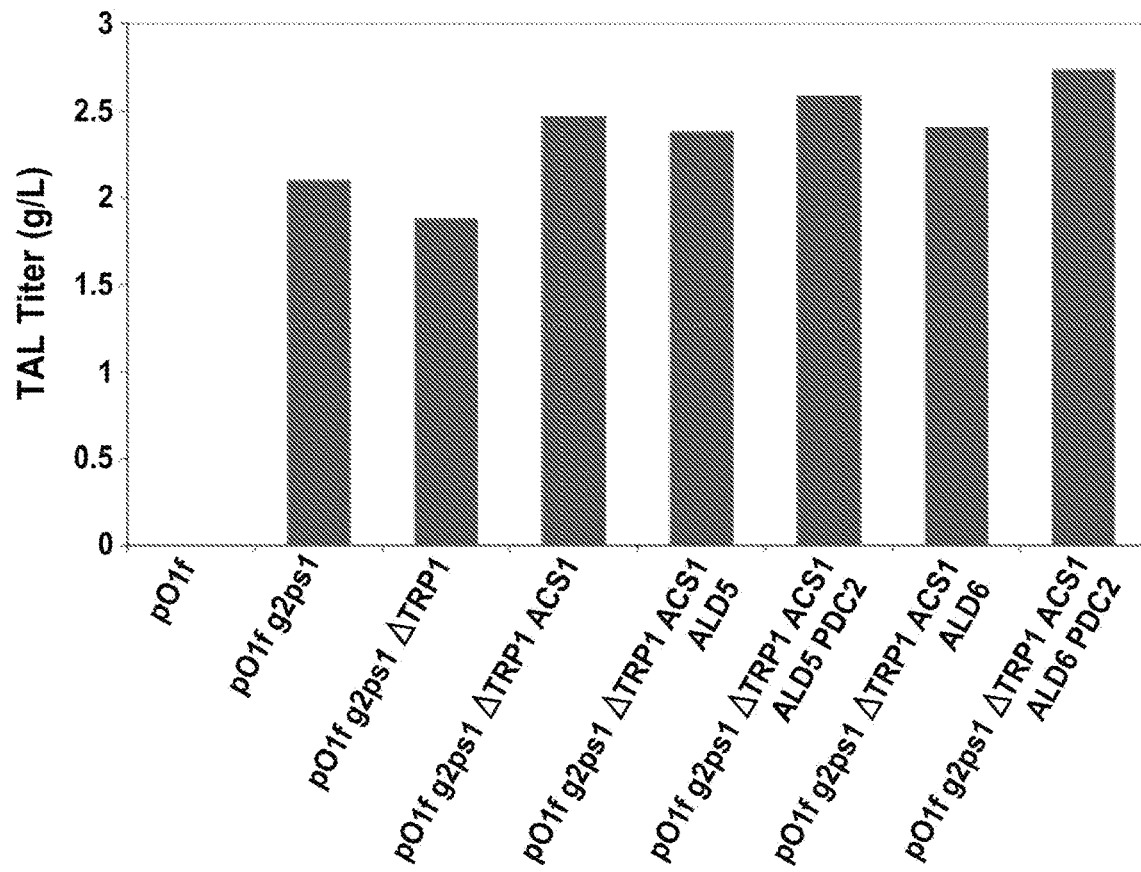
FIG. 16. Overexpression of genes through the acetate pathway (via ALD5 or ALD6) increased the titer of TAL produced in a strain background containing four copies of g2ps 1. ACC1 is overexpressed in the strains containing PDC2.
Figure 17:
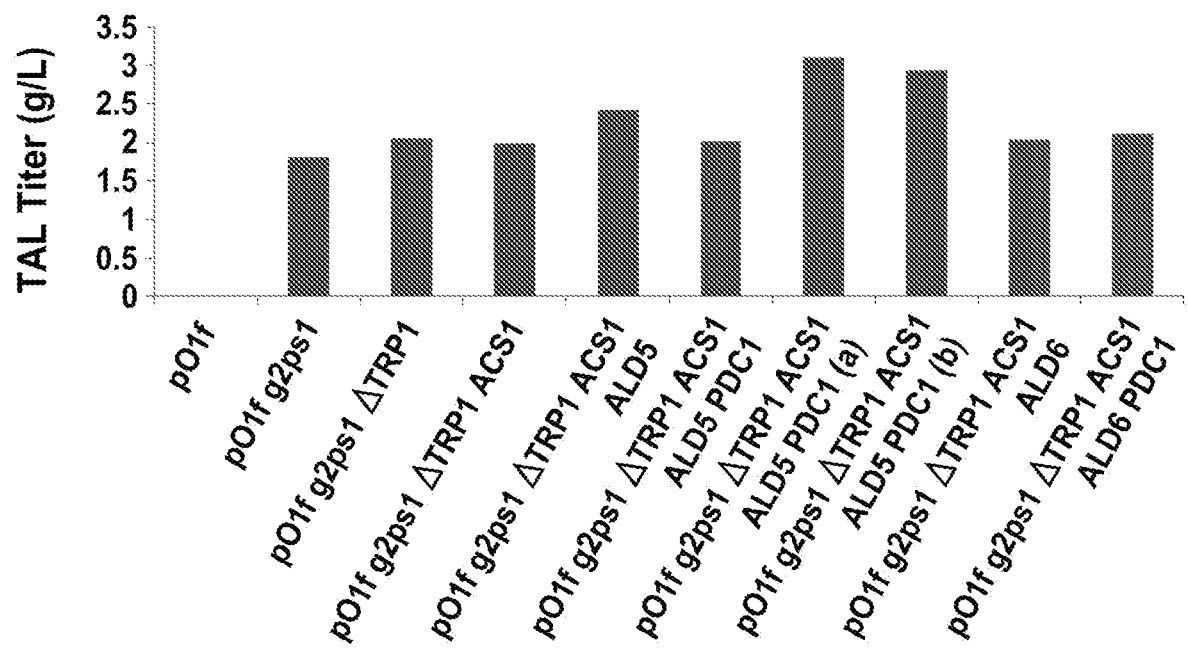
FIG. 17. Overexpression of genes through the acetate pathway (via ALD5 or ALD6) increased the titer of TAL produced in a strain background containing four copies of g2ps 1. ACC1 is overexpressed in the strains containing ALD5 and PDC1.

Some of these targets (for example, ACL1, ACL2, MAE1, PDC1, PDCE2, AceCoA, and AceCarb) were found to increase TAL levels by upwards of 2-fold (FIG. 6 and FIG. 7). In further examples, combinations of these genes are examined for additional improvements above the single gene targets.

Example 2. Analysis of Polyketide Synthases

A subset of five polyketide synthases that utilize acetyl-CoA and malonyl-CoA as the sole initiator and extender molecules were selected for testing in *Y. lipolytica*. These five targets are found in the Table 5 below with their native host, gene identifier, and target molecule listed. Each PKS was codon optimized with Blue Heron Biotech's algorithm and synthesized as a gblock (IDT). Each PKS was randomly integrated into the genome of wildtype pO1j (pO1f ΔTRP1) with a URA3 marker. Random colonies were picked from plates, glycerol stocked, and one colony of each was grown for 2 days in CSM as a starter, diluted back to an OD600 of 0.1, grown for another 2 days, and then supernatant was analyzed via LCMS. Two novel peaks were identified in the chromatogram of the supernatant of pO1j ALS. After fermentation, a visual difference in the pigment of each of the strains was evident, and each pellet was suspended in water to visualize fluorescence. There is a difference in phenotype for each strain that is further characterized to identify molecules that are being produced.

TABLE 5

Target polyketide synthase (PKS) genes used in this example

| Gene Identifier | Native Host Organism | Target Molecule | Abbreviation |
|---|---|---|---|
| CAA86219.2 | *Gerbera hybrida* | Triacetic Acid Lactone | g2ps1 |
| AY517486 | *Rheum palmatum* | Aloesone | ALS |
| JX840717-24 | *Pseudomonas fluorescens* | Phloroglucinol | PHLD |
| SCO1206 | *Streptomyces coelicolor* | 1,8-Dihydroxy-naphthalene | THNS |
| B1VLQ8 | *Streptomyces griseus* | 1,8-Dihydroxy-naphthalene | RPPA |

TAL titer can be improved by increasing flux to acetyl-CoA and malonyl-CoA precursors that are utilized by g2ps1 to make TAL. The effects of three pathways to acetyl-CoA were investigated-through acetate, through pyruvate, and through citrate with and without the overexpression of acetyl-CoA carboxylase, ACC1 to force flux from acetyl-CoA to malonyl-CoA. Each of these pathways was built in YCP63- a strain that contains four copies of g2ps1, as measured by qPCR, that were integrated into wildtype pO1f using LEU2 and URA3 markers. To increase selection availability, TRP1 was knocked out in YCP63 by creating an indel with CRISPR-Cas9. The deletion of TRP1 had a negligible effect on the production of TAL.

The acetate pathway first utilizes pyruvate decarboxylase to form acetaldehyde from pyruvate. Pyruvate decarboxylase PDC1 has been previously identified, but a putative enzyme PDC2 identified via sequence homology and was also investigated. Five separate acetaldehyde dehydrogenases were used to convert acetaldehyde to acetate (ALD1, ALD2, ALD3, ALD5, ALD6). Finally, acetyl-CoA synthetase, ACS1 was used to convert acetate to acetyl-CoA. Native genes in this acetate pathway were randomly integrated for overexpression. Completed pathways showed that together ALD5 and PDC1 with ACS1 and ACC1 produced the most TAL in four day tube fermentations (3.1 g/L with 20 g/L glucose initially fed). The second highest production of TAL was in strain pO1fg2ps1 ΔTRP1 ACS1 ALD3 PDC2 ACC1 which produced 2.7 g/L of TAL with 20 g/L glucose initially fed. No growth deficiencies are seen in any of these engineered strains indicating that *Y. lipolytica* is indeed a viable platform for the production of high titers of type III polyketides.

The pyruvate dehydrogenase complex is built of four separate genes-pyruvate dehydrogenase subunits alpha and beta (PDA1, PDB1), dihydrolipoamide acyltransferase (PDE2), and dihydrolipoamide dehydrogenase (PDE3). The entire native pyruvate dehydrogenase complex was overexpressed via random genomic integrations. With the entire pathway overexpressed, a ~20% increase in TAL titer is achieved.

Portions of the citrate pathway were selected for overexpression based on prior experience with increased fatty acid titers. Native genes encoding the two subunits of ATP citrate lyase (ACL1, ACL2) were overexpressed with AMP deaminase (AMPD) to increase acetyl-CoA available for TAL production. ACL1 and ACL2 alone do not have a positive effect on the production of TAL, but AMPD overexpressed in a strain containing the overexpressed ATP citrate lyase is analyzed for an increased production of TAL.

TABLE 6

Representative genes in pathways to acetyl-CoA

| Gene Identifier | Name | Abbreviation |
|---|---|---|
| YALI0C11407 | Acetyl-CoA Carboxylase | ACC1 |
| | Acetate Pathway | |
| YALI0D10131 | Pyruvate Decarboxylase | PDC1 |
| YALI0D06930 | Putative Pyruvate Decarboxylase | PDC2 |
| YALI0F05962 | Acetyl-CoA Synthetase | ACS1 |
| YALI0B01298 | Acetaldehyde Dehydrogenase | ALD1 |
| YALI0O03025 | Acetaldehyde Dehydrogenase | ALD2 |
| YALI0E00264 | Acetaldehyde Dehydrogenase | ALD3 |
| YALI0F23793 | Acetaldehyde Dehydrogenase | ALD4 |
| YALI0D07942 | Acetaldehyde Dehydrogenase | ALD5 |
| YALI0F04444 | Acetaldehyde Dehydrogenase | ALD6 |
| | Pyruvate Dehydrogenase Complex (PDH) | |
| YALI0F20702 | Pyruvate Dehydrogenase E1 Component Subunit Alpha | PDA1 |
| YALI0E27005 | Pyruvate Dehydrogenase E1 Component Subunit Beta | PDB1 |
| YALI0D23683 | Dihydrolipoamide Acetyltransferase | PDE2 |
| YALI0D20768 | Dihydrolipoamide Dehydrogenase | PDE3 |
| | ATP Citrate Lyase | |
| YALI0E34793 | ATP Citrate Lyase Subunit 1 | ACL1 |
| YALI0D24431 | ATP Citrate Lyase Subunit 2 | ACL2 |
| YALI0E11495 | AMP Deaminase | AMPD |

In addition to increasing the available acetyl-CoA and malonyl-CoA via overexpressions that directly affect upstream precursor formation, carbons trapped in *Yarrowia lipolytica*'s abundant fatty acid pool can be freed by overexpressing genes related to beta-oxidation and knocking out an inessential gene related to fatty acid storage. Three gene targets were selected for overexpression-peroxin 10 (PEX10), multifunctional (3-oxidation protein (MFE1), and primary oleate regulator (POR1). One target was selected for knockout-phophatidate phosphatase (PAH1). Gene overexpressions and knockouts are built in YCP63 ΔTRP1. The combination of these genes is analyzed for an increase in the acetyl-CoA freed via β-oxidation enabling the production of higher TAL titers.

TABLE 7

Additional target genes related to the upregulation of β-oxidation.
β Oxidation Upregulation

| Gene Identifier | Name | Abbreviation |
|---|---|---|
| YALI0C01023 | peroxin 10 | PEX10 |
| YALI0E15378 | multifunctional β oxidation protein (oxidoreductase and hydro-lyase) | MFE1 |
| YALI0D12628 | primary oleate regulator | POR1 |
| YALI0D27016 | phosphatidate phosphatase | PAH1 |

These additional target genes in Table 7 are assayed for their effects on increasing acetyl-CoA pools via breakdown of fatty acids to improve production of TAL.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

We claim:

1. A genetically modified oleaginous yeast cell comprising a heterologous gene encoding a heterologous Type III polyketide synthase and a gene encoding Acetyl-CoA Carboxylase (AceCarb (ACC1); YALI0C11407g), wherein the oleaginous yeast cell is *Yarrowia lipolytica*, and wherein the oleaginous yeast cell further comprises the following modifications: the overexpression of Putative Pyruvate Decarboxylase 2 (PDC2; YALI0D06930), Acetyl-CoA Synthetase 1 (ACS1; YALI0F05962), Acetaldehyde Dehydrogenase 5 (ALD5; YALI0D07942), and peroxin 10 (PEX10; YALI0C01023).

2. The yeast cell of claim 1, wherein the Type III polyketide synthase is selected from the group consisting of a CAA86219.2 gene from *Gerbera hybrida*, AY517486 gene from *Rheum palmatum*, JX840717-JX840724 gene from *Pseudomonas fluorescens*, BOLDU5 gene from *Rubus idaeus*, B1VLQ8 gene from *Streptomyces griseus*, SCO1206 from *Streptomyces coelicolor*, BAB12102.2 gene from *Humulus lupulus*, or a combination thereof.

3. The yeast cell of claim 1, wherein the heterologous gene is incorporated into a gene expression cassette comprising a promoter and the heterologous gene, wherein the gene expression cassette is integrated into the genome of the yeast cell.

4. The yeast cell of claim 1, wherein at least two copies of the heterologous gene are present in the genome of the yeast cell.

5. The yeast cell of claim 1, wherein the heterologous gene is episomally expressed from a plasmid.

6. The yeast cell of claim 1, wherein the yeast cell comprises an additional genetic modification.

7. The yeast cell of claim 6, wherein the additional genetic modification increases the acetyl-CoA or malonyl-CoA levels or fluxes.

8. The yeast cell of claim 7, wherein the additional genetic modification increases the rate of beta-oxidation to increase the acetyl-CoA or malonyl-CoA levels or fluxes.

9. The yeast cell of claim 8, wherein the additional genetic modification comprises the elimination or the reduction of *Yarrowia lipolytica* gene phosphatidate phosphatase (PAH1; YALI0D27016); and/or wherein the additional genetic modification comprises the overexpression of one or more *Yarrowia lipolytica* genes selected from the group consisting of multifunctional β oxidation protein (oxidoreductase and hydro-lyase) (MFE1; YALI0E15378), primary oleate regulator (POR1; YALI0D12628), or a combination thereof.

10. The yeast cell of claim 6, wherein the additional genetic modification comprises the elimination or the reduction of one or more *Yarrowia lipolytica* genes selected from the group consisting of Aspartyl Protease (PEP4; YALI0F27071p), Protease B Vacuolar (PRB1; YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), phosphatidate phosphatase (PAH1; YALI0D27016), or a combination thereof; and/or wherein the additional genetic modification comprises the overexpression of one or more *Yarrowia lipolytica* genes selected from the group consisting of Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Acetaldehyde Dehydrogenase 1 (ALD1; YALI0B01298), Acetaldehyde Dehydrogenase 2 (ALD2; YALI0C03025), Acetaldehyde Dehydrogenase 3 (ALD3; YALI0E00264), Acetaldehyde Dehydrogenase 4 (ALD4; YALI0F23793), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), multifunctional β oxidation protein (oxidoreductase and hydro-lyase) (MFE1; YALI0E15378), primary oleate regulator (POR1; YALI0D12628), or a combination thereof.

11. The yeast cell of claim 10, wherein the additional genetic modification comprises the elimination or the reduction of one or more *Yarrowia lipolytica* genes selected from the group consisting of Aspartyl Protease (PEP4; YALI0F27071p), Protease B Vacuolar (PRB1;

YALI0B16500p), Protease B Vacuolar (PRB1H; YALI0A06435g), Glucose-starch Glucosyltransferase Isoform 1 (GSY1; YALI0F18502p), Glucose-6-phosphate Dehydrogenase (ZWF1; YALI0E22649p), Pyruvate Carboxylase 1 (PYC1; YALI0C24101p), Phosphoenolpyruvate Carboxykinase (PCK1; YALI0C16995p), Fructose-1,6-bisphosphatase (FBP1; YALI0A15972p), Mitochondrial Carrier (YIA6; YALI0E16478g), Mitochondrial Carrier Protein (RIM2; YALI0F05500g), Alcohol Dehydrogenase 1 (ADH1; YALI0D25630p), Alcohol Dehydrogenase 2 (ADH2; YALI0E17787p), Alcohol Dehydrogenase 3 (ADH3; YALI0A16379p), C1-tetrahydrofolate Synthase (MIS1; YALI0F30745p), C1-THFS Protein C1-Tetrahydrofolate Synthase Precursor Mitochondrial (MTHFD1L; YALI0E01056g), Phosphoglucomutase (PGM2; YALI0E02090p), Glycerol-3-phosphate Dehydrogenase (GPD1; YALI0B02948p), Fatty Acid Synthase Subunit Alpha (FAS2; YALI0B19382p), Fatty Acid Synthase Subunit Beta (FAS1; YALI0B15059p), (PAH1; YALI0D27016), or a combination thereof.

12. The yeast cell of claim 10, wherein the additional genetic modification comprises the overexpression of one or more *Yarrowia lipolytica* genes selected from the group consisting of Pyruvate Decarboxylase (Pyrudecarb (PDC1); YALI0D10131p), Dihydrolipoamide Dehydrogenase (PDE3; YALI0D20768g), Dihydrolipoamide Acetyltransferase (PDE2; YALI0D23683g), Malate Dehydrogenase (MAE1; YALI0E18634p), Acetyl-CoA Synthetase (AceCoA; YALI0F05962g), Pyruvate Dehydrogenase E1 Component Subunit Alpha (PDC-E1; YALI0F20702p), ATP-Citrate Lyase Subunit 1 (ACL1; YALI0E34793p), ATP-Citrate Lyase Subunit 2 (ACL2; YALI0D24431p), AMP Deaminase (AMPD; YALI0E11495p), Acetyl-CoA hydrolase (ACH1; YALI0E30965g), Acetaldehyde Dehydrogenase 1 (ALD1; YALI0B01298), Acetaldehyde Dehydrogenase 2 (ALD2; YALI0C03025), Acetaldehyde Dehydrogenase 3 (ALD3; YALI0E00264), Acetaldehyde Dehydrogenase 4 (ALD4; YALI0F23793), Acetaldehyde Dehydrogenase 6 (ALD6; YALI0F04444), Pyruvate Dehydrogenase E1 Component Subunit Alpha (PDA1; YALI0F20702), Pyruvate Dehydrogenase E1 Component Subunit Beta (PDB1; YALI0E27005), multifunctional β oxidation protein (oxidoreductase and hydro-lyase) (MFE1; YALI0E15378), primary oleate regulator (POR1; YALI0D12628), or a combination thereof.

13. The yeast cell of claim 1, wherein the yeast cell is a PO1f strain.

14. The yeast cell of claim 1, wherein the yeast cell has been preoptimized for lipid overproduction.

15. A method for the production of a Type III polyketide comprising: 1) culturing the oleaginous yeast cell of claim 1 in a growth medium; and 2) isolating said Type III polyketide.

16. A genetically modified oleaginous yeast cell comprising a heterologous gene encoding a heterologous Type III polyketide synthase and a gene encoding Acetyl-CoA Carboxylase (AceCarb (ACC1); YALI0C11407g), wherein the oleaginous yeast cell is *Yarrowia lipolytica*, and wherein the oleaginous yeast cell further comprises the following modification: the overexpression of peroxin 10 (PEX10; YALI0C01023).

17. The yeast cell of claim 16, wherein the Type III polyketide synthase is selected from the group consisting of a CAA86219.2 gene from *Gerbera hybrida*, AY517486 gene from *Rheum palmatum*, JX840717-JX840724 gene from *Pseudomonas fluorescens*, B0LDU5 gene from *Rubus idaeus*, B1VLQ8 gene from *Streptomyces griseus*, SCO1206 from *Streptomyces coelicolor*, BAB12102.2 gene from *Humulus lupulus*, or a combination thereof.

18. The yeast cell of claim 16, wherein the heterologous gene is incorporated into a gene expression cassette comprising a promoter and the heterologous gene, wherein the gene expression cassette is integrated into the genome of the yeast cell.

19. The yeast cell of claim 16, wherein at least two copies of the heterologous gene are present in the genome of the yeast cell.

20. The yeast cell of claim 16, wherein the heterologous gene is episomally expressed from a plasmid.

21. The yeast cell of claim 16, wherein the yeast cell comprises an additional genetic modification.

22. The yeast cell of claim 21, wherein the additional genetic modification increases the acetyl-CoA or malonyl-CoA levels or fluxes.

23. The yeast cell of claim 22, wherein the additional genetic modification increases the rate of beta-oxidation to increase the acetyl-CoA or malonyl-CoA levels or fluxes.

24. The yeast cell of claim 16, wherein the yeast cell is a PO1f strain.

25. The yeast cell of claim 16, wherein the yeast cell has been preoptimized for lipid overproduction.

26. A method for the production of a Type III polyketide comprising: 1) culturing the yeast cell of claim 16 in a growth medium; and 2) isolating said Type III polyketide.

* * * * *